US012648971B2

(12) United States Patent
Blottiere et al.

(10) Patent No.: US 12,648,971 B2
(45) Date of Patent: Jun. 9, 2026

(54) USE OF ADLERCREUTZIA BACTERIA FOR THE TREATMENT OF INFLAMMATORY DISEASES

(71) Applicants: Institut National de Recherche Pour L'Agriculture, L'Alimentation et L'Environnement, Paris (FR); INSTITUT NATIONAL DES SCIENCES ET INDUSTRIES DU VIVANT ET DE L'ENVIRONNEMENT, Palaiseau (FR); ENTEROME, Paris (FR)

(72) Inventors: Hervé Blottiere, Nantes (FR); Philippe Gerard, Palaiseau (FR); Sebastian Burz, Garat (FR); Florian Plaza Oñate, Marcoussy (FR)

(73) Assignees: INSTITUT NATIONAL DE RECHERCHE POUR L'AGRICULTURE L'ALIMENTATION ET L'ENVIRONNEMENT, Paris (FR); INSTITUT NATIONAL DES SCIENCES ET INDUSTRIES DU VIVANT ET DE L'ENVIRONNEMENT, Palaiseau (FR); ENTEROME, Paris (FR); UNIVERSITE PARIS-SACLAY, Gif-sur-Yvette (FR)

( * ) Notice: Subject to any disclaimer, the term of this patent is extended or adjusted under 35 U.S.C. 154(b) by 359 days.

(21) Appl. No.: 18/022,763

(22) PCT Filed: Aug. 24, 2021

(86) PCT No.: PCT/EP2021/073417
§ 371 (c)(1),
(2) Date: Feb. 23, 2023

(87) PCT Pub. No.: WO2022/043335
PCT Pub. Date: Mar. 3, 2022

(65) Prior Publication Data
US 2023/0310519 A1      Oct. 5, 2023

(30) Foreign Application Priority Data

Aug. 25, 2020    (EP) ..................................... 20305950

(51) Int. Cl.
| | |
|---|---|
| *A61K 35/741* | (2015.01) |
| *A61K 35/00* | (2006.01) |
| *A61K 45/06* | (2006.01) |
| *A61P 1/16* | (2006.01) |
| *A61P 29/00* | (2006.01) |

(52) U.S. Cl.
CPC ............ *A61K 35/741* (2013.01); *A61K 45/06* (2013.01); *A61P 1/16* (2018.01); *A61P 29/00* (2018.01); *A61K 2035/115* (2013.01)

(58) Field of Classification Search
None
See application file for complete search history.

(56) References Cited

U.S. PATENT DOCUMENTS

2018/0250350 A1* 9/2018 Sokol ........................ A61P 1/00

FOREIGN PATENT DOCUMENTS

WO      WO-2018065132 A1 *  4/2018  ................ A61P 3/10

OTHER PUBLICATIONS

Written Opinion in International Application No. PCT/EP2021/073417, Dec. 22, 2021, pp. 1-6.
Bajer, L. et al. "P0974 Distinct gut microbiota profiles in patients with primary sclerosing cholangitis and ulcerative colitis" *United European Gastroenterology Journal*, Oct. 1, 2017, pp. A501-A502, vol. 5, No. 5.
Bajer, L. et al. "Distinct gut microbiota profiles in patients with primary sclerosing cholangitis and ulcerative colitis" *World Journal of Gastroenterology*, Jul. 7, 2017, pp. I-IV and 4548-4558, vol. 23, No. 25.

* cited by examiner

*Primary Examiner* — Brian Gangle
(74) *Attorney, Agent, or Firm* — SALIWANCHIK, LLOYD & EISENSCHENK

(57) ABSTRACT

The present invention relates to the preventive or curative treatment of inflammatory diseases such as non-alcoholic fatty liver disease and inflammatory bowel diseases using *Adlercreutzia* bacteria.

21 Claims, 10 Drawing Sheets

Specification includes a Sequence Listing.

USE OF ADLERCREUTZIA BACTERIA FOR THE TREATMENT OF INFLAMMATORY DISEASES

CROSS-REFERENCE TO RELATED APPLICATION

This application is the U.S. national stage application of International Patent Application No. PCT/EP2021/073417, filed Aug. 24, 2021.

REFERENCE TO SEQUENCE LISTING

The Sequence Listing for this application is labeled "Seq-List.txt" which was created on Feb. 8, 2023 and is 2,257 bytes. The entire content of the sequence listing is incorporated herein by reference in its entirety.

FIELD OF THE INVENTION

The present invention relates to the field of medicine and in particular to compositions comprising bacterial probiotics, and more particularly to compositions comprising live biotherapeutic products, for the preventive or curative treatment of inflammatory diseases such as non-alcoholic fatty liver disease and inflammatory bowel diseases.

BACKGROUND OF THE INVENTION

Inflammation is part of the complex biological response of body tissues to harmful stimuli such as physical (e.g. burns, injury), chemical (e.g. toxins, alcohol) or biological (e.g. pathogens) stimuli, or stimuli interpreted by the body to have a potentially harmful effect.

Inflammation is thus a protective response involving immune cells, blood vessels, and molecular mediators to eliminate the initial cause of cell injury, clear out necrotic cells and damaged tissues and initiate tissue repair. While after injury, inflammation is a normal and healthy response, inflammatory disorders result in the immune system attacking the body's own cells or tissues leading to abnormal inflammation. Inflammatory abnormalities are a large group of disorders that underlie a vast variety of human diseases such as inflammatory bowel diseases (IBD) and non-alcoholic fatty liver disease (NAFLD). In several pathologies, this inflammation is associated with rupture of symbiosis including modification of the gut microbiota (dysbiosis) with loss of richness and increased gut permeability and oxidative stress.

Non-alcoholic fatty liver disease (NAFLD) is the most common liver disease in developed countries. NAFLD includes the subtypes of simple steatosis, i.e. excessive fatty accumulation in the hepatocytes, also named nonalcoholic fatty liver (NAFL), and nonalcoholic steatohepatitis (NASH), i.e. steatosis accompanied by evidence of inflammation and cell injury with or without fibrosis. NASH, the more aggressive form of NAFLD, may progress to cirrhosis, liver failure, and hepatocellular carcinoma. Extensive researches have been conducted on NAFLD. In particular, it was found that immune and inflammatory pathways have a central role in the pathogenesis of NAFLD and that the key pro-inflammatory signaling pathways in NASH are nuclear factor-kappa B (NF-κB) and c-Jun N-terminal kinase (JNK) (Farrell et al. Gut Liver. 2012 April; 6(2): 149-171). Recent studies also revealed the links between the intestinal microbiota and NAFLD (Safari et al. Cell Mol Life Sci. 2019 April; 76(8):1541-1558.) as well as the possibility to use gut microbiome biomarkers as tools for diagnosis of liver cirrhosis (Qin et al. Nature. 2014 Sep. 4; 513(7516):59-64) or to distinguish mild/moderate NAFLD from advanced fibrosis (Loomba et al. Cell Metab. 2017 May 2; 25(5):1054-1062.e5).

The first line of management in NASH remains lifestyle modifications, mainly sustained weight loss and increased physical activity. Some medications are currently under investigation such as anti-inflammatory, anti-caspase, anti-oxidant, anti-fibrotic and anti-LPS agents (Oseini et al. Liver Int. 2017 January; 37(Suppl 1): 97-103). However, to date, despite the burden to the public health system and a better understanding of the pathogenesis and progression of NASH, there are no current approved therapies for this disease.

Inflammatory bowel diseases (IBD) is a general term used to identify a group of chronic inflammatory disorders of the gastrointestinal (GI) tract including Crohn's disease and ulcerative colitis. While the exact cause of IBD is not entirely understood, it is known to involve genetic predisposition, dysbiosis of the gut microbiota and environmental influences. IBD is characterized by the repeated alternating cycles of clinical relapse and remission. In the absence of adequate treatment, IBD leads to chronic inflammation and thus to irreversible intestinal damages. Crohn's disease can affect any part of the GI tract but most commonly affects the end of the small intestine (the ileum) where it joins the beginning of the colon. Crohn's disease may appear in "patches," affecting some areas of the GI tract while leaving other sections completely untouched. In Crohn's disease, the inflammation may extend through the entire thickness of the bowel wall. Ulcerative colitis is limited to the large intestine (colon) and the rectum. The inflammation occurs only in the innermost layer of the lining of the intestine. It usually begins in the rectum and lower colon, but may also spread continuously to involve the entire colon. In some individuals, it is difficult to determine whether their IBD is Crohn's disease or ulcerative colitis. In these rare cases, people are given the diagnosis of indeterminate colitis (IC).

Despite increased understanding of the underlying disease process there is no cure. Medications currently available such as anti-inflammatory drugs, immune system suppressors and antibiotics, are used to reduce the inflammation that triggers signs and symptoms. However, the same treatments have significant potential toxicity including increased infection risk, steroid toxicity, increased risk of malignancy, and many patients can lose response when treatments are used long term.

Thus, there is still a strong need of new medications to be used in the prevention or treatment of inflammatory diseases such as inflammatory bowel diseases (IBD) and non-alcoholic fatty liver disease (NAFLD).

SUMMARY OF THE INVENTION

The inventors herein found that *Adlercreutzia* bacteria can be used in the treatment or prevention of inflammatory diseases, and in particular in the treatment or prevention of NAFLD and IBD. Indeed, they demonstrated that these bacteria not only exhibit anti-inflammatory effects but can also induce a reduction in weight gain and some steatosis markers in a mouse model of hepatic steatosis.

Accordingly, the present invention relates to a composition comprising an *Adlercreutzia* bacterium and/or a culture extract thereof, for use in the treatment of an inflammatory disease.

In particular, the bacterium may be selected from the group consisting of *Adlercreutzia equolifaciens, Adlercreutzia caecimuris, Adlercreutzia mucosicola* and *Adlercreutzia muris*, preferably may be an *Adlercreutzia equolifaciens* bacterium.

Preferably, the comprises an *Adlercreutzia* bacterium, more preferably a living *Adlercreutzia* bacterium. In particular, the composition may comprise a living *Adlercreutzia* bacterium selected from the group consisting of *Adlercreutzia equolifaciens, Adlercreutzia caecimuris, Adlercreutzia mucosicola* and *Adlercreutzia muris*, preferably a living *Adlercreutzia equolifaciens* bacterium.

Alternatively or additionally, the composition may comprise a culture extract of said *Adlercreutzia* bacterium. In particular, the culture extract may be selected from the group consisting of culture supernatant, cell debris, cell walls and protein extracts. Preferably, the culture extract is culture supernatant.

The composition of the invention may comprise one or several strains of *Adlercreutzia* and/or a culture extract of one or several strains of *Adlercreutzia*, said strains of *Adlercreutzia* being preferably selected from the group consisting of *Adlercreutzia equolifaciens, Adlercreutzia caecimuris, Adlercreutzia mucosicola* and *Adlercreutzia muris*, and combinations thereof.

The composition of the invention may further comprise at least one additional active ingredient. In particular, said additional active ingredient may be an additional bacterial probiotic, preferably selected from the group consisting of bacteria belonging to the genera *Allobaculum, Akkermansia, Anaerostipes, Bifidobacterium, Bacillus, Propionibacterium, Bacteroides, Eubacterium, Enterococcus, Ruminococcus, Roseburia* and *Faecalibacterium, Escherichia coli*, and lactic acid bacteria, in particular lactic acid bacteria belonging to the genera *Lactobacillus* and *Streptococcus*.

The composition of the invention may also further comprise or may be used in combination with one or several drugs useful in the treatment of the disease.

Preferably, the composition of the invention is to be administered by oral or rectal route.

Preferably, the disease is selected from the group consisting of non-alcoholic fatty liver disease and associated disorders, and inflammatory bowel diseases. More preferably, the disease is selected from non-alcoholic fatty liver disease or associated disorders, said disorders being preferably selected from the group consisting of cholangitis, obesity, insulin resistance, glucose intolerance, type 2 diabetes and coronary heart diseases. Even more preferably, the disease may be selected from non-alcoholic fatty liver disease or associated disorders, said disorders being selected from the group consisting of obesity, insulin resistance, glucose intolerance, type 2 diabetes and coronary heart diseases.

In particular, the disease may be a non-alcoholic fatty liver disease selected from the group consisting of nonalcoholic fatty liver (NAFL), nonalcoholic steatohepatitis (NASH), cirrhosis, liver failure and hepatocellular carcinoma, preferably selected from the group consisting of nonalcoholic steatohepatitis (NASH), cirrhosis, liver failure and hepatocellular carcinoma, preferably is nonalcoholic steatohepatitis (NASH).

In some embodiments, the disease may be selected from the group consisting of cholangitis, obesity, insulin resistance, glucose intolerance, type 2 diabetes and coronary heart diseases, and the subject to be treated may be suffering from non-alcoholic fatty liver disease, preferably is suffering from nonalcoholic steatohepatitis (NASH). Preferably, the disease may be selected from the group consisting of obesity, insulin resistance, glucose intolerance, type 2 diabetes and coronary heart diseases, and the subject to be treated is suffering from non-alcoholic fatty liver disease, preferably is suffering from nonalcoholic steatohepatitis (NASH).

In other embodiments, the disease may be an inflammatory bowel disease, preferably selected from the group consisting of Crohn's disease, ulcerative colitis, indeterminate colitis (IC), other noninfective gastroenteritis, enteritis, enterocolitis and colitis, and pouchitis, more preferably selected from Crohn's disease and ulcerative colitis.

DETAILED DESCRIPTION OF THE INVENTION

Figure 1:
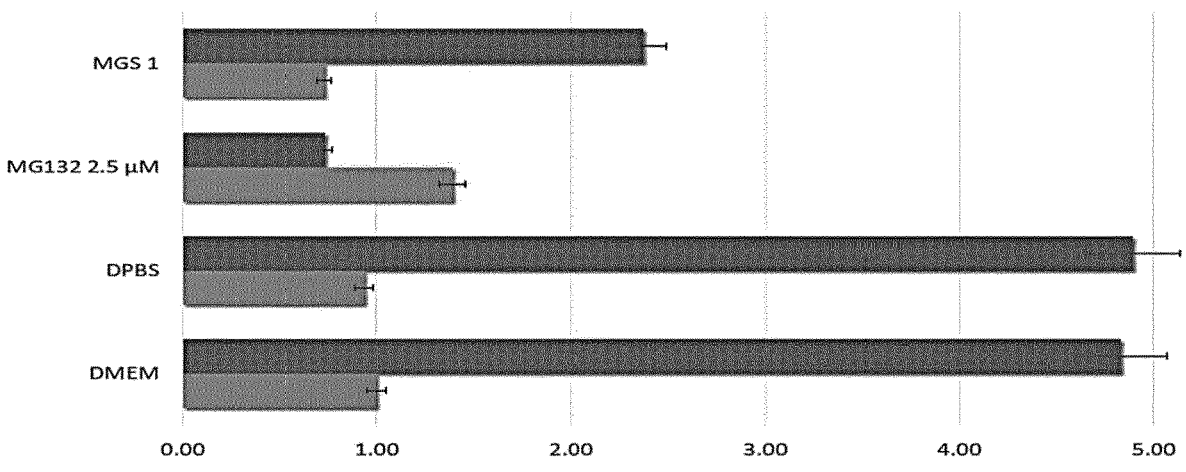
FIG. 1: *Adlercreutzia equolifaciens* (MGS1) inhibit NF-KB activity on HepG2 NF-KB reporter cell line. NF-kB activity is measured in the presence (top bars) or absence (bottom bars) of TNF-alpha. Values represent fold increase of NF-kB activity in unstimulated cells (DMEM alone). MG132 (a proteasome inhibitor) is a positive control of inhibition of inflammation induced by TNF.

The inventors herein demonstrated that a bacterium belonging to the genus *Adlercreutzia*, and in particular *Adlercreutzia equolifaciens*, exhibits anti-inflammatory effects in vitro and in vivo. They also demonstrated that this bacterium administered by gavage to mice in a model of hepatic steatosis induced by the transfer of gut microbiota from a NASH patient and subjected to a hyperlipidic, fructose-rich diet, induced a reduction in weight gain and some steatosis markers especially hyperglycemia and liver expression of the pro-inflammatory cytokine, interleukin-6 (IL-6).

Accordingly, in a first aspect; the present invention relates to a composition comprising an *Adlercreutzia* bacterium and/or a culture extract thereof, for use in the treatment of an inflammatory disease. It also relates to the use of a composition comprising an *Adlercreutzia* bacterium and/or a culture extract thereof, for the manufacture of a medicament for the treatment of an inflammatory disease. It further relates to a method for treating an inflammatory disease in a subject, said method comprising administering to the subject a composition comprising an *Adlercreutzia* bacterium and/or a culture extract thereof.

*Adlercreutzia* (NCBI Taxonomy ID: 447020) is a genus of Gram-positive, obligately anaerobic, asaccharolytic, non-spore-forming, non-motile coccobacilli. This genus was firstly described by Maruo et al. (Maruo et al. Int. J. Syst. Evol. Microbiol. (2008) 58:1221-1227), the definition was amended by Nouioui et al. (Nouioui et al. Front. Microbiol. (2018) 9:2007) and then by Stoll et al. (Stoll et al. Int. J. Syst. Evol. Microbiol. (2021) 71:004814). The type species of this genus is *Adlercreutzia equolifaciens* (NCBI Taxonomy ID: 446660).

Bacteria of this genus typically exhibit the following features: (i) the predominant isoprenologues are methylmenaquinone-6 and dimethylmenaquinone-6, (ii) the G+C content is about 60-70%, (iii) whole-cell hydrolysates contain DL- or LL-2,6-diaminoheptanedioic acid (DL- or LL-A2pm) as the diamino acid and galactose with either ribose or glucose, and (iv) major fatty acids are either $C_{16:0}$, iso-$C_{15:0}$ or $C_{16:0}$, iso-C17:0 and $C_{18:1}$ $\omega$9c.

Preferably, the bacterium used in the present invention comprises a 16S rRNA gene having at least 90%, at least 91%, at least 92%, at least 93%, at least 94%, at least 95%, at least 96%, at least 97%, at least 98%, at least 99% or 100% sequence identity with SEQ ID NO: 1 (NCBI Reference Sequence: NR_121696.1). More preferably, the bacterium used in the present invention comprises a 16S rRNA gene having at least 95%, at least 96%, at least 97%, at least 98%, at least 99% or 100% sequence identity with SEQ ID NO: 1. Even more preferably, the bacterium used in the present invention comprises a 16S rRNA gene having at least 96%, at least 97%, at least 98%, at least 99% or 100% sequence identity with SEQ ID NO: 1.

In particular, the bacterium used in the present invention may be a bacterium from a species selected in the group consisting of *Adlercreutzia equolifaciens, Adlercreutzia caecimuris, Adlercreutzia mucosicola* and *Adlercreutzia muris.*

*Adlercreutzia equolifaciens* species was described by Maruo et al. (Maruo et al. Int. J. Syst. Evol. Microbiol. (2008) 58:1221-1227). The type strain of *Adlercreutzia equolifaciens* is FJC-B9 (CCUG 54925T, DSM 19450T, JCM 14793T, *Adlercreutzia equolifaciens* subsp. *equolifaciens*) which was isolated from feces of a healthy human. *Adlercreutzia equolifaciens* bacteria are commercially available, for example from DSMZ collection (Leibniz Institute DSMZ-German Collection of Microorganisms and Cell Cultures GmbH) under accession number DSM 19450, from JCM collection (Japan Collection of Microorganisms, RIKEN BioResource Research Center) under accession number JCM 14793 or from CCUG collection (Culture Collection University of Gothenburg, Goteborg, Sweden) under accession number 54925. An *Adlercreutzia equolifaciens* subspecies, namely *Adlercreutzia equolifaciens* subsp. *celatus* (also named *Asaccharobacter celatus*), was also described by Minamida et al. (Minamida et al., 2008, Int. J. Syst. Evol. Microbiol. 58, 1238-1240). The type strain of *Adlercreutzia equolifaciens* subsp. *celatus* is do03 (AHU 1763, DSM 18785, JCM 14811). *Adlercreutzia equolifaciens* subsp. *celatus* bacteria are commercially available, for example from DSMZ collection (Leibniz Institute DSMZ-German Collection of Microorganisms and Cell Cultures GmbH) under accession number DSM 18785 or from JCM collection (Japan Collection of Microorganisms, RIKEN BioResource Research Center) under accession number JCM 14811.

*Adlercreutzia caecimuris* species (also named *Enterorhabdus caecimuris*) was described by Clavel et al. (Clavel et al. 2010, Int. J. Syst. Evol. Microbiol. 60, 1527-1531). The type strain of this species is B7 (DSM 21839, CCUG 56815). *Adlercreutzia caecimuris* bacteria are commercially available, for example from DSMZ collection (Leibniz Institute DSMZ-German Collection of Microorganisms and Cell Cultures GmbH) under accession number DSM 21839 or from CCUG collection (Culture Collection University of Gothenburg, Göteborg, Sweden) under accession number 56815.

*Adlercreutzia mucosicola* species (also named *Enterorhabdus mucosicola*) was described by Clavel et al. (Clavel et al. 2009, Int. J. Syst. Evol. Microbiol. 59, 1805-1812.). The type strain of this species is Mt1B8 (DSM 19490, CCUG 54980). *Adlercreutzia mucosicola* bacteria are commercially available, for example from DSMZ collection (Leibniz Institute DSMZ-German Collection of Microorganisms and Cell Cultures GmbH) under accession number DSM 19490 or from CCUG collection (Culture Collection University of Gothenburg, Göteborg, Sweden) under accession number 54980.

*Adlercreutzia muris* species (also named *Enterorhabdus muris*) was described by Lagkouvardos et al. (Lagkouvardos et al. 2016, Nat. Microbiol. 1, 1-15). The type strain of this species is WCA-131-CoC-2 (DSM 29508, KCTC 15543). *Adlercreutzia muris* bacteria are commercially available, for example from DSMZ collection (Leibniz Institute DSMZ-German Collection of Microorganisms and Cell Cultures GmbH) under accession number DSM 29508 or from KCTC collection (Korean Collection for Type Cultures) under accession number 15543.

The bacterium used in the present invention does not belong to *Parvibacter caecicola* species previously named *Adlercreutzia caecicola*. Indeed, it has been shown that this species does not belong to the genus *Adlercreutzia* (Stoll et al. Int. J. Syst. Evol. Microbiol. (2021) 71:004814).

In a particular embodiment, the bacterium used in the present invention is a bacterium selected from the group consisting of *Adlercreutzia equolifaciens* (including *Adlercreutzia equolifaciens* subsp. *equolifaciens* and *Adlercreutzia equolifaciens* subsp. *celatus*), *Adlercreutzia caecimuris*, *Adlercreutzia mucosicola* and *Adlercreutzia muris*, preferably selected from the group consisting of *Adlercreutzia equolifaciens, Adlercreutzia caecimuris* and *Adlercreutzia mucosicola*.

In a more particular embodiment, the bacterium used in the present invention is selected from the group consisting of FJC-B9 (*Adlercreutzia equolifaciens* subsp. *equolifaciens* DSM 19450), do03 (*Adlercreutzia equolifaciens* subsp. *celatus* DSM 18785), B7 (*Adlercreutzia caecimuris* DSM 21839), Mt1B8 (*Adlercreutzia mucosicola* DSM 19490) and WCA-131-CoC-2 (*Adlercreutzia muris* DSM 29508) strains, or mutants thereof, preferably selected from the group consisting of FJC-B9 (*Adlercreutzia equolifaciens* subsp. *equolifaciens* DSM 19450), do03 (*Adlercreutzia equolifaciens* subsp. *celatus* DSM 18785), B7 (*Adlercreutzia caecimuris* DSM 21839) and Mt1B8 (*Adlercreutzia mucosicola* DSM 19490) strains, or mutants thereof.

As used herein, the term "mutant" should be understood as a strain derived, or a strain which can be derived, from a strain as disclosed (or the mother strain) by means of e.g. genetic engineering, radiation and/or chemical treatment. The mutant can also be a spontaneously occurring mutant. It is preferred that the mutant is a functionally equivalent mutant, e.g. a mutant that has substantially the same, or improved, properties (preferably anti-inflammatory properties) as the mother strain. The use of such mutants is part of the present invention. Especially, the term "mutant" refers to a strain obtained by subjecting a strain as disclosed to any conventionally used mutagenization treatment including treatment with a chemical mutagen such as ethane methane sulphonate (EMS) or N-methyl-N'-nitro-N-nitroguanidine (NTG), UV light, or to a spontaneously occurring mutant. A mutant may have been subjected to several mutagenization treatments (a single treatment should be understood one mutagenization step followed by a screening/selection step), but it is presently preferred that no more than 20, or no more than 10, or no more than 5, treatments (or screening/selection steps) are carried out. In a presently preferred mutant, less than 1%, less than 0.1%, less than 0.01%, less than 0.001% or even less than 0.0001% of the nucleotides in the bacterial genome have been mutated, i.e. substituted, inserted or deleted, compared to the mother strain. Preferably, the genome of the mutant has at least 99% sequence identity to the genome of the mother strain and said mutant exhibits anti-inflammatory activity.

In preferred embodiments, the bacterium used in the present invention is an *Adlercreutzia equolifaciens* bacterium.

*Adlercreutzia* bacteria can be cultured in anaerobic conditions, at 37° C. and in a suitable medium easily chosen by the skilled person. Examples of suitable media include, but are not limited to, Wilkins-Chalgren anaerobe broth completed with 0.5% arginine, Chopped Meat Medium, PYG medium, Acidaminococcus *Fermentans* medium with rumen fluid and Columbia Blood Medium.

As demonstrated in the experimental section, *Adlercreutzia* bacteria used in the present invention exhibit anti-inflammatory activity. This activity can be assess using any suitable assay known by the skilled person. In particular, this activity can be measured by assessing the ability of the bacterium to inhibit activation of the NF-KB pro-inflammatory pathway by TNF-α, for example using reporter cells designed for the monitoring of bioactive TNF-α in biological samples by assessing NF-KB activation. In particular, the capacity of the bacterium to inhibit TNF-α NF-KB activation can be measured by using an assay as described in the examples. Briefly, *Adlercreutzia* bacteria are grown until DO=0.3; bacterial cultures are then centrifuged at 5000 g for 10 minutes and cell pellets are resuspended in 1 ml of DPBS. NF-KB reporter cells HepG2/kb-seap or HT-29-NF-kB cl25 as described in Lakhdari et al., (2010, PLoS One 5), are seeded at 40,000 cells per well, into 96-wells plates and incubated 24 hours. These cells are then stimulated for 24 hours with 10 µL of resuspended bacterial pellet, for a final volume of 100 µl per well (i.e. 10% vol/vol), in the presence or absence of TNF-α (10 ng/mL final). SEAP in the supernatant is then revealed using the standard protocol.

Preferably, the bacterium used in the present invention induces at least 20%, at least 30%, at least 40% or at least 50% inhibition of TNF-α NF-κB activation. More preferably, the bacterium used in the present invention induces at least 40% or at least 50% inhibition of TNF-α NF-κB activation. In particular, this inhibition can be measured using the in vitro assay described above.

As demonstrated in the experimental section in a mouse model of hepatic steatosis, *Adlercreutzia* bacteria used in the present invention may also be able to reduce weight gain, to slow induced hyperglycemia, to reduce the full caecum weight, to increase the amount of butyrate in cecal content, to reduce the proportion of branched chain fatty acids (iso-butyrate and iso-valerate) in cecal content and/or to reduce the expression of pro-inflammatory cytokine Interleukine-6 (IL-6) in the caecum and the liver. In particular, *Adlercreutzia* bacteria used in the present invention may be able to increase the amount of butyrate in cecal content, to reduce the proportion of branched chain fatty acids (iso-butyrate and iso-valerate) in cecal content and/or to reduce the expression of IL-6 in the caecum and the liver by at least 10%, preferably at least 20%, 30% or 40%, in a subject. Preferably, these variations are assessed at least one month, preferably one month, after administration of the composition of the invention.

The composition of the invention may comprise one or several strains of *Adlercreutzia* and/or a culture extract of one or several strains of *Adlercreutzia*. In particular the composition of the invention may comprise one or several strains of *Adlercreutzia* selected from the group consisting of *Adlercreutzia equolifaciens, Adlercreutzia caecimuris,*

*Adlercreutzia mucosicola* and *Adlercreutzia muris*, and/or a culture extract of one or several of these strains. More particularly, the composition of the invention may comprise one or several strains of *Adlercreutzia equolifaciens* and/or a culture extract of one or several strains of *Adlercreutzia equolifaciens*.

Preferably, the composition of the invention comprises at least one *Adlercreutzia equolifaciens* bacterium and/or a culture extract thereof.

In an embodiment, the composition of the invention comprises an inactivated *Adlercreutzia* bacterium, i.e. at least one inactivated *Adlercreutzia* strain. Preferably, said strain is selected from the group consisting of *Adlercreutzia equolifaciens, Adlercreutzia caecimuris, Adlercreutzia mucosicola* and *Adlercreutzia muris*. More preferably, said strain is a *Adlercreutzia equolifaciens* bacterium. In this embodiment, it is not excluded that the composition also comprises other bacterial or culture components such as living bacteria and/or cell debris and/or culture medium. Inactivated bacteria are not able to grow when cultured in a suitable medium. Preferably, inactivated bacteria are killed bacteria. Bacteria can be inactivated by any means known by the skilled person such as heat treatment (e.g. pasteurization) or irradiation. Inactivated bacteria can be preserved before administration by any method known by the skilled person such as lyophilization and subsequent storage, preferably at temperatures ranging from +4° C. to −80° C.

In another embodiment, the composition of the invention comprises a culture extract of an *Adlercreutzia* bacterium, preferably a culture extract of a bacterium selected from the group consisting of *Adlercreutzia equolifaciens, Adlercreutzia caecimuris, Adlercreutzia mucosicola* and *Adlercreutzia muris*, more preferably a culture extract of an *Adlercreutzia equolifaciens* bacterium. As used herein, the term "culture extract" refers an extract obtained from the culture of an *Adlercreutzia* bacterium, preferably the culture of a bacterium selected from the group consisting of *Adlercreutzia equolifaciens, Adlercreutzia caecimuris, Adlercreutzia mucosicola* and *Adlercreutzia muris*, more preferably the culture of an *Adlercreutzia equolifaciens* bacterium, in a suitable cell culture medium and under suitable conditions, said extract exhibiting anti-inflammatory activity. The anti-inflammatory activity of the extract may be assessed as described above. The extract may be any fraction obtained from the culture or from bacterial cells, such as a culture supernatant, cell debris, cell walls, DNA or RNA extracts, protein extracts, and in general any preparation derived from bacterial cells or cell culture by chemical, physical and/or enzymatic treatments. Preferably, the culture extract is selected from the group consisting of culture supernatant, cell debris, cell walls and protein extracts, in particular from the group consisting of cell debris, cell walls and protein extracts. In a preferred embodiment, the culture extract is culture supernatant. The culture extract may be free of intact bacterial cells or may contain some residual intact bacterial cells, preferably less than $10^3$ cells per mL. The culture extract may be diluted or concentrated before use.

In embodiments wherein the composition comprises a culture extract of several strains of *Adlercreutzia*, said culture extract may be obtained from a co-culture of said strains or by mixing a culture extract of each of the strains.

In preferred embodiments, the composition of the invention comprises a living *Adlercreutzia* bacterium, i.e. at least one living *Adlercreutzia* strain. Preferably, said strain is selected from the group consisting of *Adlercreutzia equolifaciens, Adlercreutzia caecimuris, Adlercreutzia mucosicola* and *Adlercreutzia muris*, more preferably is a *Adlercreutzia*

*equolifaciens* bacterium. In this embodiment, it is not excluded that the composition also comprises other bacterial or culture components such as dead bacteria and/or cell debris and/or culture medium. By "living bacteria", it is to be understood that the integrity of the cells is maintained and that cellular processes occur or can occur if the bacteria are cultured in the suitable medium and conditions. A living bacterium can be re-seeded in a suitable culture medium and grow under suitable conditions. Living bacteria may be preserved before administration by freezing with liquid nitrogen, gradual freezing or lyophilization and subsequent storage, preferably at temperatures ranging from +4° C. to −80° C.

In a particular embodiment, the composition comprises a cell culture comprising an *Adlercreutzia* bacterium. As used herein, the term "cell culture" refers to the mix of bacterial cells and liquid broth used to culture these cells. In particular, the cell culture may be obtained by inoculating a suitable liquid broth with a living *Adlercreutzia* bacterium, incubating said mix in suitable conditions (in particular in anaerobic conditions), and recovering cell culture.

The composition of the invention may comprise one or several *Adlercreutzia* bacteria, preferably living *Adlercreutzia* bacteria, i.e. one or several strains belonging to *Adlercreutzia* genus, preferably selected from the group consisting of *Adlercreutzia equolifaciens, Adlercreutzia caecimuris, Adlercreutzia mucosicola* and *Adlercreutzia muris*. Preferably, at least one of these bacteria belongs to *Adlercreutzia equolifaciens* species.

The composition of the invention may further comprise at least one additional active ingredient, in particular at least one additional bacterial probiotic and/or at least one prebiotic and/or at least one drug useful in the treatment of an inflammatory disease.

In particular, the composition may further comprise one or several additional bacterial probiotics. Preferably, the composition comprises less than 50, less than 20, less than 10, or less than 5 additional bacterial probiotics. The term "bacterial probiotic" has its general meaning in the art and refers to a useful bacterium that can bring a beneficial action to the host health, i.e. which is applicable to the prevention, treatment or cure of a disease or condition of the host, preferably a human being. This term may refer to a dead or living bacterium. Preferably, this term refers to a living bacterium (also named live biotherapeutic product).

Preferably, one or several of these additional bacterial probiotics exhibit anti-inflammatory activity. This activity may be provided by the living bacterial probiotic, by a secretory substance produced by said bacterial probiotic, or by a dead microbial body or homogenate of said bacterial probiotic.

Preferably, said one or several bacterial probiotics are selected from the group consisting of bacteria belonging to the genera *Allobaculum* (e.g. *Allobaculum stercoricanis*), *Akkermansia* (e.g. *Akkermansia muciniphila*), *Anaerostipes* (e.g. *Anaerostipes hadrus, Anaerostipes caccae* and *Anaerostipes butyraticus*), *Bifidobacterium, Bacillus* (e.g. *Bacillus subtilis* and *Bacillus clausii*), *Propionibacterium, Bacteroides, Eubacterium, Enterococcus, Ruminococcus* (e.g. *Ruminococcus gnavus*), *Roseburia* (e.g. *Roseburia hominis*) and *Faecalibacterium* (e.g. *Faecalibacterium prausnitzii*), *Escherichia coli*, and lactic acid bacteria, in particular lactic acid bacteria belonging to the genera *Lactobacillus* (e.g. *Lactobacillus reuteri, Lactobacillus plantarum, Lactobacillus taiwanensis, Lactobacillus johnsonii, Lactobacillus animalis, Lactobacillus murinus, Lactobacillus salivarius, Lactobacillus gasseri, Lactobacillus bulga-*

11                                                                12

*ricus*, and *Lactobacillus delbrueckii* subsp. *Bulgaricus*) and *Streptococcus* (e.g. *Streptococcus thermophilus*).

Alternatively or additionally, the composition of the invention may further comprise one or several prebiotics. As used here, a "prebiotic" refers to an ingredient that can induce specific changes in both the composition and/or activity of the administered probiotic(s) and/or gastrointestinal microbiome that may confer benefits to the host. Preferably, the prebiotic can be degraded by the probiotic(s), preferably by the *Adlercreutzia* bacterium, and may increase the shelf life of said probiotic(s) after administration to the patient. Examples of prebiotics include, but are not limited to, complex carbohydrates, polyphenols, amino acids, peptides, minerals, or other nutritional components essential for the survival of the probiotic(s). In particular embodiments, the prebiotic is a complex carbohydrate that can be digested by a human or an animal but can be used by at least one bacterium present in the composition of the invention, preferably by an *Adlercreutzia* bacterium. In particular, the prebiotic may selected from the group consisting of inulin, inositol, tagatose, lactulose, alpha-glucan oligosaccharide, trans-galacto-oligosaccharides (TOS), fructo-oligosaccharides (FOS), galacto-oligosaccharides (GOS), xylo-oligosaccharides (XOS) and a mixture thereof.

Alternatively or additionally, the composition of the invention may further comprises one or several drugs useful in the treatment of the inflammatory disease, in particular one or several drugs in the treatment of a disease selected from the group consisting of non-alcoholic fatty liver disease and associated disorders, and inflammatory bowel diseases.

Examples of drugs useful in the treatment of inflammatory bowel diseases include, but are not limited to, corticosteroids, 5-aminosalicylates, immunosuppressors such as cyclosporin, azathioprine, 6-mercaptopurine, methotrexate, anti-TNF agents (such as infliximab, adalimumab, golimumab, certolizumab), anti-integrin agents (such as natalizumab, vedolizumab) anti-IL12 and/or -IL23 antibodies (such as ustekinumab), JAK inhibitors (such as tofacitinib), antibiotics, anti-diarrheals, pain relievers, iron supplements, vitamin B-12, calcium and vitamin D.

Examples of drugs useful in the treatment of non-alcoholic fatty liver disease include, but are not limited to, PPAR agonists, GLP-1 agonists, DPPIV inhibitors, and vitamin E.

In some embodiments, the composition of the invention is to be used in combination with one or several drugs useful in the treatment of the disease, in particular with one or several of the drugs as disclosed above. Said drug can be administered simultaneously or sequentially with the composition of the invention.

In a particular embodiment, the composition consists essentially in one or several *Adlercreutzia* bacteria, preferably one or several living *Adlercreutzia* bacteria, and/or culture extract thereof. As used herein, the term "consists essentially in" is intended to refer to a composition that does not comprise any other active ingredient, in particular any other active ingredient as defined above.

In another particular embodiment, the composition comprises one or several *Adlercreutzia* bacteria, preferably one or several living *Adlercreutzia* bacteria, and/or culture extract thereof and does not comprise any other bacterial probiotic.

In another particular embodiment, the composition comprises one or several *Adlercreutzia* bacteria, preferably one or several living *Adlercreutzia* bacteria, and/or culture extract thereof, and one or several additional bacterial probiotics, preferably less than 50, less than 20, less than 10, or less than 5 additional bacterial probiotics.

The composition of the invention may be a pharmaceutical composition, a food composition or a food supplement.

In preferred embodiments, the composition of the invention is a pharmaceutical composition comprising an *Adlercreutzia* bacterium as defined above, preferably a living *Adlercreutzia* bacterium, and/or a culture extract thereof, and a pharmaceutically acceptable excipient. More preferably, the composition of the invention is a pharmaceutical composition comprising an *Adlercreutzia* bacterium as defined above, and a pharmaceutically acceptable excipient. Even more preferably, the composition of the invention is a pharmaceutical composition comprising a living *Adlercreutzia* bacterium as defined above, and a pharmaceutically acceptable excipient.

As used herein, the term "pharmaceutically acceptable" refer to molecular entities and compositions that do not produce an adverse, allergic or other untoward reaction when administered to a mammal, especially a human, as appropriate. A pharmaceutically acceptable excipient refers to a non-toxic solid, semi-solid or liquid filler, diluent, encapsulating material or formulation auxiliary of any type. The pharmaceutically acceptable excipients that can be used in the composition according to the invention are well known to the skilled person and may vary according to the disease to be treated and the administration route.

The composition of the invention can be administered by any method suitable for depositing in the gastrointestinal tract, preferably the small intestine and/or the colon, of the subject to be treated. In particular, the composition can be administered by enteral or parenteral route, preferably by oral, sublingual, subcutaneous, intramuscular, intravenous, transdermal, local or rectal administration route. Preferably, the composition of the invention is administered, or is adapted to be administered, by rectal or oral route.

In an embodiment, the pharmaceutical composition is to be administered by oral route. For oral administration, the pharmaceutical composition can be formulated into conventional oral dosage forms such as tablets, capsules, powders, granules and liquid preparations such as syrups, elixirs, and concentrated drops. Nontoxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatin, sugars such as lactose or dextrose, and natural or synthetic gums can be used as binders. Disintegrants may also be necessary in the tablets to facilitate break-up of the tablet. Disintegrants include starches, clays, celluloses, algins, gums and crosslinked polymers. Moreover, lubricants and glidants may also be included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants. Well-known thickening agents may also be added to compositions such as corn starch, agar, natural or synthetic gums, resins, methylcellulose, sodium carboxymethylcellulose, guar, xanthan and the like. Preservatives may also be included in the composition, including methylparaben, propylparaben, benzyl alcohol and ethylene diamine tetraacetate salts.

Preferably, for oral administration, the composition is in a gastro-resistant oral form allowing the active compounds contained in the composition, to pass the stomach and be released into the intestine. The material that can be used in enteric coatings includes, for example, alginic acid, cellulose acetate phthalate, plastics, waxes, shellac and fatty acids (e.g. stearic acid or palmitic acid).

In another embodiment, the pharmaceutical composition is to be administrated by rectal route. Suitable rectal-route forms include, but are not limited to, suppository and enema. In particular, the active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Compositions according to the invention may be formulated to release the active ingredients substantially immediately upon administration or at any predetermined time or time period after administration.

In others embodiments, the composition may be a food composition or a food supplement.

By "food composition" is meant any composition comprising food ingredients such as macronutrients, micronutrients, vitamins and/or minerals. The food composition may be intended for human or animal consumption and may be a liquid, paste or solid. Examples of food compositions include, but are not limited to dairy products such as cheese, butter, cream, yoghurt, fermented milk, ice cream, cooked products such as bread, biscuits and cakes, fruit products such as fruit juice, fruit compote or fruit paste, soy food products, starch-based food products, edible oil compositions, spreads, breakfast cereals, infant formula, food bars (e.g. cereal bars, breakfast bars, energy bars, nutrition bars), chewing gum, beverages, drinking supplements (powders to be added to a beverage).

As used herein, the term "food supplement" refers to any composition which is formulated and administered separately from other foods to complement the nutritional intakes of a subject, i.e. a human or an animal. This supplement may be in any suitable form well known to those skilled in the art, preferably in the form of dietetic food or oral supplementation.

The composition of the invention is used in the treatment of an inflammatory disease, preferably a liver or intestinal inflammatory disease.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of the disease or symptoms associated with it. In other embodiments, this term refers to minimizing the spread or worsening of the disease resulting from the administration of one or more therapeutic agents, e.g. the composition of the invention, to a subject with such a disease.

The disease to be treated is preferably selected from the group consisting of non-alcoholic fatty liver disease and associated disorders, and inflammatory bowel diseases.

In an embodiment, the disease to be treated is selected from non-alcoholic fatty liver disease or associated disorders. In particular, said associated disorders may be selected from the group consisting of cholangitis, obesity, insulin resistance, glucose intolerance, type 2 diabetes and coronary heart diseases. Preferably, in embodiments wherein the disease to be treated is selected from the group consisting of cholangitis, obesity, insulin resistance, glucose intolerance, type 2 diabetes and coronary heart diseases, the subject to be treated is suffering from non-alcoholic fatty liver disease, preferably is suffering from nonalcoholic steatohepatitis (NASH).

In a particular embodiment, the disorder associated to non-alcoholic fatty liver disease is not cholangitis. Thus, in this embodiment, the disease to be treated may be selected from non-alcoholic fatty liver disease or associated disorders and said associated disorders may be selected from the group consisting of obesity, insulin resistance, glucose intolerance, type 2 diabetes and coronary heart diseases. Preferably, in embodiments wherein the disease to be treated is selected from the group consisting of obesity, insulin resistance, glucose intolerance, type 2 diabetes and coronary heart diseases, the subject to be treated is suffering from non-alcoholic fatty liver disease, preferably is suffering from nonalcoholic steatohepatitis (NASH).

Non-alcoholic fatty liver disease includes the subtypes of simple steatosis, i.e. nonalcoholic fatty liver (NAFL), steatosis accompanied by evidence of inflammation and cell injury with or without fibrosis, i.e. nonalcoholic steatohepatitis (NASH) as well as more aggressive form such as cirrhosis, liver failure and hepatocellular carcinoma.

In a particular embodiment, the disease to be treated is a non-alcoholic fatty liver disease selected from the group consisting of nonalcoholic fatty liver (NAFL), nonalcoholic steatohepatitis (NASH), cirrhosis, liver failure and hepatocellular carcinoma.

In a preferred embodiment, the disease to be treated is selected from the group consisting of non-alcoholic steatohepatitis (NASH), cirrhosis, liver failure and hepatocellular carcinoma.

In a more preferred embodiment, the disease to be treated is nonalcoholic steatohepatitis (NASH).

In some other embodiments, the disease is an inflammatory bowel disease. As used herein, "inflammatory bowel diseases" or "IBD" refers to any of a variety of diseases characterized by inflammation of all or part of the intestines. Examples of inflammatory bowel diseases include, but are not limited to, Crohn's disease (such as enteritis, ileitis, colitis, ileocolitis, gastroduodenal and perianal Crohn's), ulcerative colitis (such as ulcerative enterocolitis, ulcerative ileocolitis, ulcerative proctitis, ulcerative rectosigmoiditis, pseudopolyposis of colon, mucosal proctocolitis, and left-sided or extensive ulcerative colitis), indeterminate colitis (IC), other noninfective gastroenteritis, enteritis, enterocolitis and colitis (such as non-microscopic colitis including collagenous colitis and lymphocytic colitis, radiation-induced, toxic-induced, allergic-induced, dietetic-induced, ischemic, eosinophilic gastroenteritis, enteritis, enterocolitis or colitis, segmental colitis associated with diverticula, diversion colitis and Behcet's colitis) as well as pouchitis.

Preferably, the inflammatory bowel disease is selected from the group consisting of Crohn's disease and ulcerative colitis, more preferably is ulcerative colitis.

The composition of the invention may be used in combination with an anti-inflammatory diet or a low carb diet. In particular, such anti-inflammatory diet may comprise 1) avoiding pro-inflammatory food, in particular such as refined carbohydrates, fried foods, soft drinks and other sweetened beverages, red meat and processed meat; 2) favoring the intake of anti-inflammatory food, such as olive oil, green leafy vegetables like spinach or kale, nuts like almonds and walnuts, fatty fish like salmon, mackerel, tuna and sardines, fruits like strawberries, blueberries, cherries, oranges, apples and tomatoes.

The subject to be treated with the composition of the invention is an animal, preferably a mammal. In an embodiment, the subject is a domestic or farmed animal such as dogs, cats, cows, sheep, horses or rodents. In a preferred embodiment, the subject is a human, including adult, child, newborns and human at the prenatal stage. As used herein, the terms "subject", "individual" and "patient" are interchangeable.

The dosage of *Adlercreutzia* bacterial cells and/or culture extract may be appropriately adjusted according to criteria such as age, symptoms, body weight, and intended application such as to obtain a therapeutically efficient amount. The term "therapeutically efficient amount" as employed herein refers to the amount necessary for having a beneficial impact on the disease to be treated, i.e. to prevent, remove or reduce at least one deleterious effect of the disease.

In embodiments wherein the disease to be treated is IBD, a therapeutically efficient amount is preferably defined as the amount necessary for having an impact on intestinal inflammation or any symptom of the disease such as diarrhea, fever or pain.

In embodiments wherein the disease to be treated is NAFLD, and in particular NASH, a therapeutically efficient amount is preferably defined as the amount necessary for having an impact on liver steatosis (accumulation of lipid droplet and triglyceride content), on fibrosis and/or on liver inflammation, e.g. reducing at least one inflammatory marker such as IL-6.

In some embodiments, the composition of the invention may comprise from $10^3$ to $10^{11}$ living *Adlercreutzia* bacterial cells, preferably selected from the group consisting of *Adlercreutzia equolifaciens, Adlercreutzia caecimuris, Adlercreutzia mucosicola* and *Adlercreutzia muris* bacterial cells, more preferably *Adlercreutzia equolifaciens* bacterial cells, per mg of composition and/or from 0.001 mg to 1000 mg of dried or lyophilized culture supernatant per g of composition.

In particular, the amount of *Adlercreutzia* bacteria, preferably selected from the group consisting of *Adlercreutzia equolifaciens, Adlercreutzia caecimuris, Adlercreutzia mucosicola* and *Adlercreutzia muris* bacteria, more preferably *Adlercreutzia equolifaciens* bacteria, ingested per day may be from $1\times10^6$ to $1\times10^{11}$ CFU/body, preferably $0.1\times10^9$ to $10\times10^9$ CFU/body, and more preferably $0.3\times10^9$ to $5\times10^9$ cells/body.

The content of *Adlercreutzia* bacteria, preferably selected from the group consisting of *Adlercreutzia equolifaciens, Adlercreutzia caecimuris, Adlercreutzia mucosicola* and *Adlercreutzia muris* bacteria, more preferably *Adlercreutzia equolifaciens* bacteria, contained in an orally ingested composition of the invention may be for example from 1% to 100% (w/w, i.e. bacteria dry weight/total dry weight of the composition), preferably from 1% to 75% (w/w), and more preferably from 5% to 50% (w/w).

The composition of the invention may be administered as a single dose or in multiple doses. In particular, depending on the subject's age or physiological condition, daily doses may be divided to facilitate administration, for example with one administration in the morning and another in the evening.

In some embodiments, the composition is to be administered regularly, preferably between every day and every month, more preferably between every day and every two weeks, more preferably between every day and every week. In some particular embodiments, the composition is to be administered every day.

The duration of treatment with the composition of the invention may be comprised between 1 day and several years, preferably between 1 day and one year, more preferably between 1 day and 6 months.

All the references cited in this description are incorporated by reference in the present application. Others features and advantages of the invention will become clearer in the following examples which are given for purposes of illustration and not by way of limitation.

EXAMPLES

Example 1: In Vitro Model on Cell Culture

Materials and Methods

Cell Culture and Reagents

HepG2 cells were grown in DMEM (Sigma) with 2 mM L-glutamine, 50 IU/mL penicillin, 50 μg/mL streptomycin and 10% heat-inactivated fetal calf serum (FCS—Lonza) in a humidified 5% $CO_2$ atmosphere at 37° C. Absence of *mycoplasma* contamination was controlled using the Myco-Alert kit (Lonza).

Commensal Strains and Preparation of Conditioned Media

*Adlercreutzia equolifasciens* (DSM 19450) bacteria were grown in anaerobic Wilkins Chalgren medium completed with 0.5% arginine (WCA0.5A) at 37° C. using the Hungate culture method (Hungate RE (1950) Bacteriol Rev 14: 1-49).

At the end of the incubation period, DO of 0.3 or above, bacterial cultures were centrifuged at 5000 g for 10 minutes. Cell pellets were resuspended in 1 ml DPBS.

Analyses of NF-κB Activation—SEAP Reporter Assay

Construction and validation of the NF-κB reporter clones HepG2/kb-seap were done as described previously (Lakhdari et al. (2010) PLoS One 5). For each experiment, reporter cells were seeded at 40 000 cells per well, into 96-wells plates and incubated 24 hours. Then cells were stimulated for 24 hours with 10 μl of tested resuspended bacterial pellet, for a final volume of 100 μl per well (i.e. 10% vol/vol), in the presence or absence of TNF-α (10 ng/ml final). MG-132 (Millipore/Calbiochem used at a final concentration of 2.5 μmol/L) was used as a positive control of NF-kB pathway inhibition.

SEAP in the supernatant was revealed using the Quanti-Blue™ reagent (Invivogen) according to the manufacturer's protocol and quantified at $OD_{655nm}$. All measurements were performed using a microplate reader (Infinite 200, Tecan). Cell viability was controlled using the MTS assay (CellTiter 96 Aquous One, Promega) following manufacturer's instruction.

Statistical Analysis

Results are expressed as mean±SD. Data were analyzed using Student's t test.

Results

As illustrated on FIG. 1, cells used in the test responded strongly to TNF-alpha by activating the NF-κB pro-inflammatory pathway. The bottom bars correspond to untreated cells (no TNF activation). Two controls (DMEM and DPBS) were also present. These controls show that when TNF is added the NF-κB pathway is activated by a 5-fold factor. MG132 corresponds to a positive inhibition control. When this molecule was added, NF-kB pathway activation was completely inhibited. It was also checked that cell viability was no affected by the bacteria.

Concerning *A. equolifaciens*, in the absence of TNF-alpha, the bacterial pellet resuspended in DPBS (MGS1), mildly inhibited the basal activity. However, in the presence of TNF-alpha, a strong inhibition was observed. The bacterial pellet induced about 50% inhibition of inflammation triggered by the addition of TNF-alpha.

These results highlight the anti-inflammatory potential of the bacteria.

Example 2: Animal Model

Materials and Methods

Clinical Cohort

A cohort of 20 NAFLD patients with moderate obesity, aged 62 on average was recruited; a liver biopsy determined a diagnosis of NAFL or NASH. All subjects gave their informed consent for inclusion before they participated in the study. The study was conducted in accordance with the Declaration of Helsinki, and the protocol was approved by the French CPP Ethics Committee. A NASH donor was selected among the 20 donors.

Animal Experimentation

Procedures were performed according to the European Guidelines for the Care and Use of Laboratory Animals and approved by the French Veterinary Authorities. The experimental protocol was agreed by the French Ministère de l'Education Nationale, de l'Enseignement Supérieur et de la Recherche. Twenty four specific pathogen free (SPF) C57Bl/6J male mice, 7 weeks old, were purchased from Charles River Laboratories, France, from different litters. On arrival, animals were housed under controlled conditions of temperature, hygrometry and 12 h light/dark cycle in a SPF facility at INRAE, Jouy-en-Josas (Unité Expérimentale d'Infectiologie des Rongeurs et Poissons). They were individually weighted, microchipped and randomly housed in new cages, 4 mice per cage; they received a conventional gamma-irradiated 45 kGy mice control diet (CD) SAFEA03 R03-40 ad libitum (3.24 kcal/g: 14% energy from fat, 25% energy from proteins, 61% energy from carbohydrates, (SAFE, Augy, France, CD). On day 6 after arrival, feces of the mice were individually harvested (basal microbiota). Then, they received in the autoclaved drinking water for 2 weeks a mixture of broad spectrum antibiotics (Vancomycin 45 µL/mL, Streptomycin 1 mg/mL, Colistin 1 mg/mL and Ampicillin 1 mg/mL) ad libitum, to clean their endogenous microbiota as previously described by Zhang et al. (FASEB J. 2019 June; 33(6):7126-7142.). The irradiated litter and food were replaced every 48 h, each cage with filter cover was autoclaved once a week. On day 16, an all-bacteria-qPCR was performed to verify complete absence of detectable bacteria in the feces (threshold of 99.99% depletion was considered to be equivalent to germ-free mice). The stools of the selected human individuals were inoculated (200 µL per mouse) by two gavages at 48 h intervals (day 21 and 22). Fecal transplants contained more than 70% of viable bacteria as shown by flow cytometry. The mice received the fecal microbiota from a selected NASH patient, they were subsequently referred to as "NASH". Mice were fed ad libitum for 10 weeks a high-fat, high-fructose diet (2HFD), to induce NAFLD, consisting of a gamma-irradiated 45 kGy high-fat diet D12492, containing 31.7% lard and 3.2% soybean oil (5.24 kcal/g: 60% energy from fat, 20% energy from protein, 20% energy from carbohydrate, Research Diets, Lynge, Denmark) associated with a 30% (w/v) final high fructose drinking solution (1.2 kcal/mL). Fructose solution was made by dissolution of D(−)-Fructose >99.5% purchased from Roth Sochiel (Lauterbourg, France) in autoclaved tap water, final solution was then 0.22 µm filtered sterilized (2HFD).

Body weight, food and liquid consumption were monitored weekly. Mice stools were collected individually at five time points: on day 6 (basal), 16 (after 2 weeks antibiotics treatment), 27 (1 week after fecal microbiota transplant), 55 (1 month after fecal microbiota transplant), 84 (1 week before the end of the experiment). On day 90, mice were euthanatized, liver, epididymal and mesenteric adipose tissue, caecum and blood were then harvested.

Preparation and Preservation of Fecal Transplants

Preservation solution in MD diluent was furnished by MaaT Pharma (Lyon, France). Fecal transplant was prepared as previously described (Burz et al., *Sci. Rep., vol.* 9, no. 1, p. 8897, December 2019).

Short Chain Fatty Acids Quantification of Cecal Contents

Measurement of the short-chain fatty acids (SCFA) and branched-chain fatty acids from mice cecal contents was performed on day 90 using gas chromatography as previously described by Lan et al. (*Br. J. Nutr., vol.* 100, no. 6, pp. 1251-1259 December 2008), with slight modifications. The analyses were performed on an Agilent (Les Ulis, France) gas-chromatograph equipped with a split-splitless injector 7850 and ionization flame detector. Carrier gas (H2) flow rate was 10 mL/min and inlet, column and detector temperatures were 200, 100 and 240° C., respectively. Data were collected and peaks integrated using OpenLab Chem station software (Les Ulis, France).

Oral Glucose Tolerance Test (OGTT)

Fasting glycemia and insulinemia measurements as well as OGTT were performed on day 70, i.e. after 7 weeks of the 2HFD regimen, 21 days before euthanasia. After 6 h of fasting, a glucose solution (2 g glucose/kg body weight) was administered by oral gavage. Blood glucose levels at time 0 (fasting glycemia, determined before glucose gavage) and 15, 30, 60, 90 and 120 min after glucose gavage were analyzed using an Accu-Check glucometer (Roche, Meylan, France). The glucose levels were plotted against time, and the AUC (area under curve) were calculated. The plasma insulin concentrations at times 0 (fasting insulinemia) and after 30 min, were analyzed in venous blood (collected in EDTA-coated tubes), harvested from marginal tail vein, using a mouse-specific Insulin ELISA Kit (Merck Millipore, St Quentin en Yvelines, France). Insulin resistance was estimated by homeostasis model assessment (HOMA-IR index) and calculated according to the following formulas:

$$\text{HOMA-IR (fasting)} = \text{fasting glucose (mmol/L)} \times \text{fasting insulin (mU/L)}/22.5.$$

$$\text{HOMA-IR (non fasting)} = \text{non fasting glucose (mmol/L)} \times \text{non fasting insulin (mU/L)}/22.5.$$

Real-Time Quantitative Polymerase Chain Reaction (qPCR)

A ¼ portion of the left liver lobe and a piece of caecum, was stored in RNAlater™ stabilization solution (Invitrogen, Carlsbad, CA, USA) at −80° C. until further analysis. Total RNA was extracted with RNAeasy Plus Mini Kit (Qiagen, Hilden, Germany). RNA integrity and concentration were checked with RNA 6000 Nano chips on an Agilent 2100 bioanalyser (Agilent Technologies, Amsterdam, Netherlands). Total RNA (10 µg per reaction) was reverse transcribed into complementary DNA using high-capacity cDNA reverse transcription kit (Applied Biosystems, Thermofisher Scientific, Foster City, California, USA) according to the manufacturer's instructions. Real time qPCR was performed on an Applied biosystem step one plus machine.

The relative expressions of IL-6 gene were normalized to two housekeeping genes: GAPDH and Actb (glyceraldehyde-3-phosphate dehydrogenase, actin beta).

Statistical Analysis

Datasets normality was tested using the D'Agostino & Pearson normality test. Normally distributed data with equal group variances were expressed as mean±standard errors of the mean (SEM). Non-normally distributed data, or belonging to unequal group variances, were expressed as medians (interquartile ranges). The level of significance was set at $p < 0.05$ (*$p < 0.05$, $p < 0.01$, *$p < 0.001$).

Statistical comparisons done for diet impact and for microbiota impact and subsequent unpaired Student t test or unpaired Mann-Whitney test were used. Calculations were performed with R 3.5 software and GraphPad Prism software (version 7.00, La Jolla, CA, USA).

Results

The effect of *A. equolifaciens* given by oral gavage (MGS1) used as a biotherapeutic agent was evaluated in a mouse model of hepatic steatosis, i.e. C57Bl/6J SPF male mice treated with antibiotics and receiving the gut microbiota of patients with NASH and receiving a diet enriched in fat and fructose (high fat high fructose—HFHF). The mice were force-fed daily with *A. equolifaciens* resuspended in PBS. The control group received a gavage with PBS.

Figure 2A:
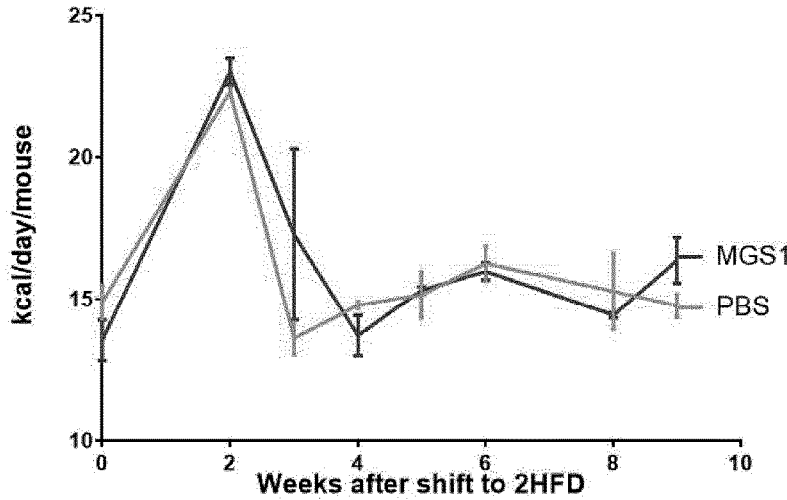
FIG. 2: *Adlercreutzia equolifaciens* gavage reduces weight gain. A—Caloric intake by mice along time after switch to high fat high fructose diet (2HFD). B—Average weight of mice along time. top graph, mean of mice receiving PBS as gavage. bottom graph, mean of mice receiving *Adlercreutzia equolifaciens* (MGS1).
Figure 2B:
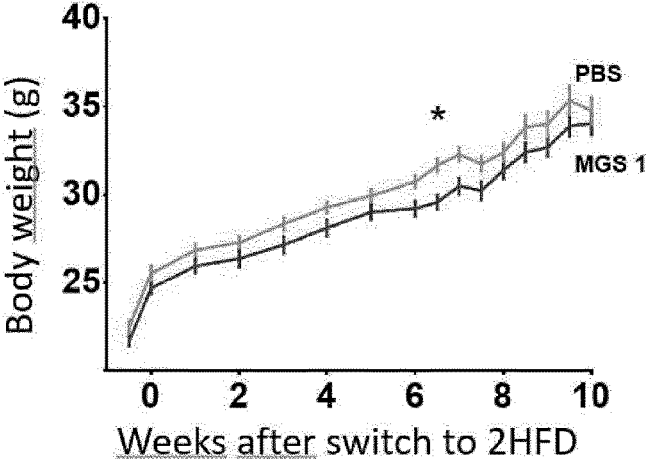
Figure 3:
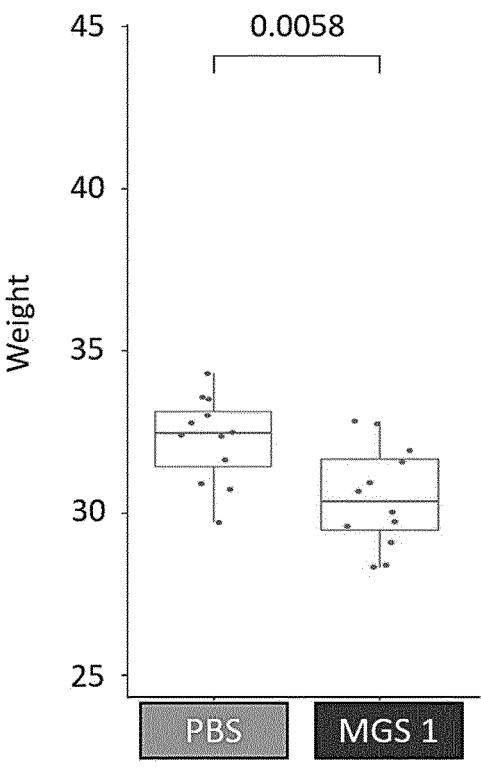
FIG. 3: *Adlercreutzia equolifaciens* gavage reduces weight gain. Weight of mice at the end of the experience. Left, mean of mice receiving PBS as gavage. Right, mean of mice receiving *Adlercreutzia equolifaciens* (MGS1).

Food consumption was similar in the two groups (FIG. 2A). However, all along the 10 weeks of experimental procedure, the gavage with *A. equolifaciens* allowed to reduce weight gain (FIGS. 2B and 3).

Figure 4:
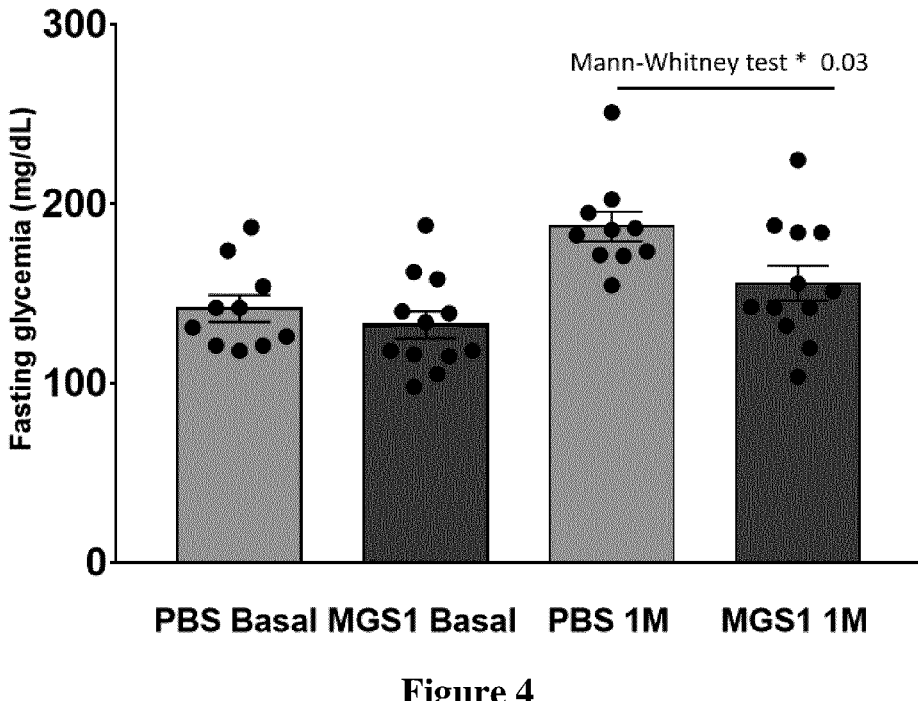
FIG. 4: *Adlercreutzia equolifaciens* gavage reduces fasting hyperglycemia. Fasting glycemia of mice at the beginning of the experience (basal) and 1 month after gavage (1M). Bars 1 and 3, mean of mice receiving PBS as gavage. Bars 2 and 4, mean of mice receiving *Adlercreutzia equolifaciens* (MGS1).
Figure 5A:
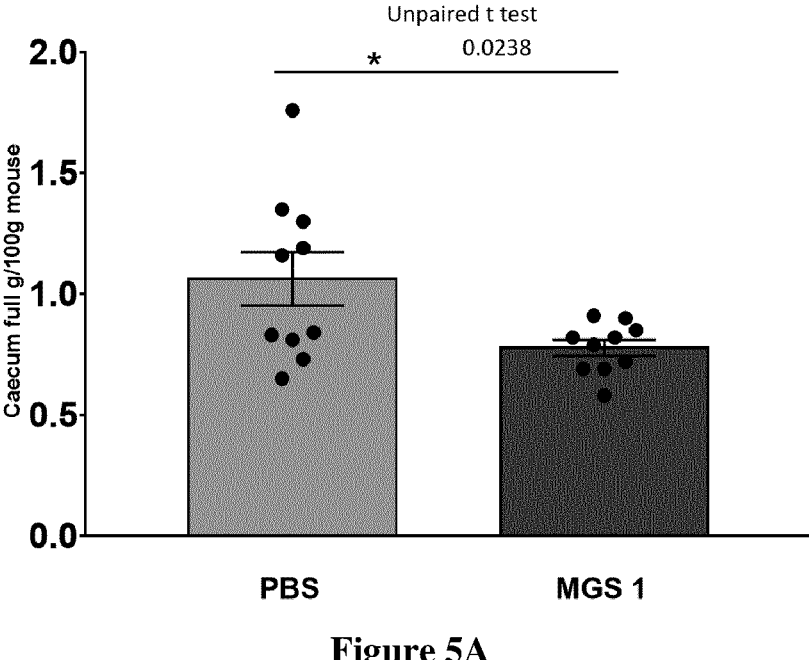
FIG. 5: *Adlercreutzia equolifaciens* gavage modulates caecum weight and caecal SCFA concentration. A—Weight of caecum/mouse weight at the end of the experience. B—Total SCFA concentration/g of caecum content. C—Butyrate concentration/g of caecum content. D—Isovalerate concentration/g of caecum content. E—Isobutyrate concentration/g of caecum content. Left, mean of mice receiving PBS as gavage. Right, mean of mice receiving *Adlercreutzia equolifaciens* (MGS1).
Figure 5B:
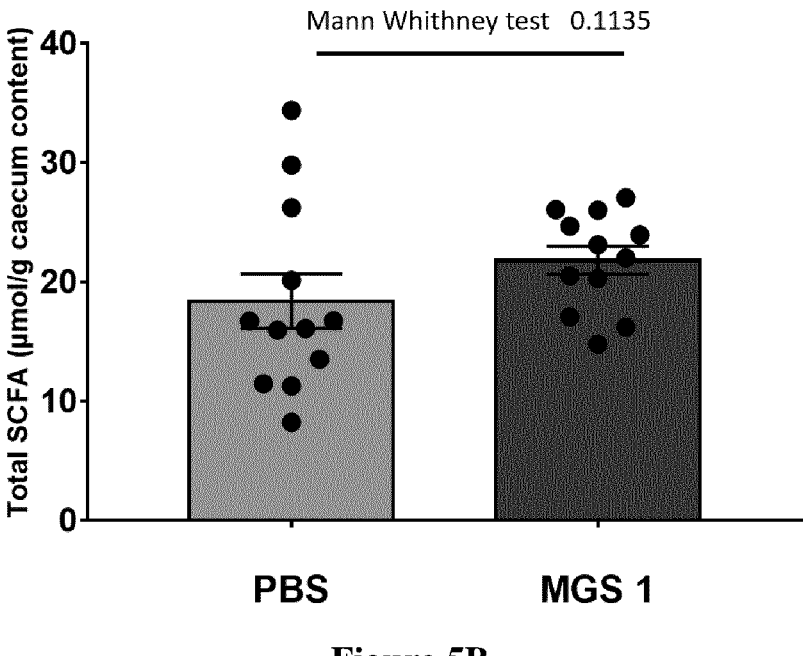
Figure 5C:
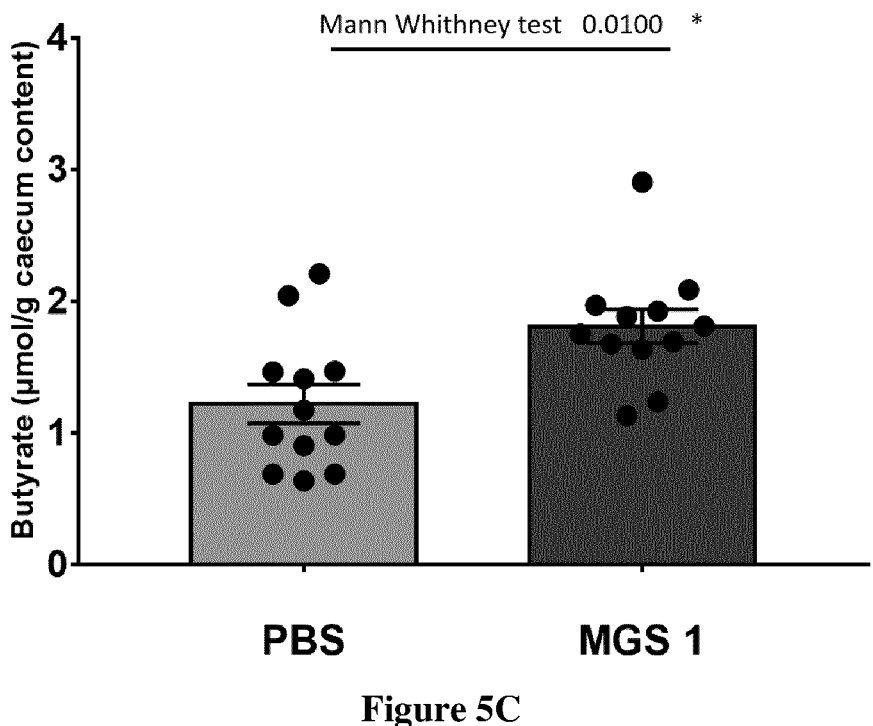
Figure 5D:
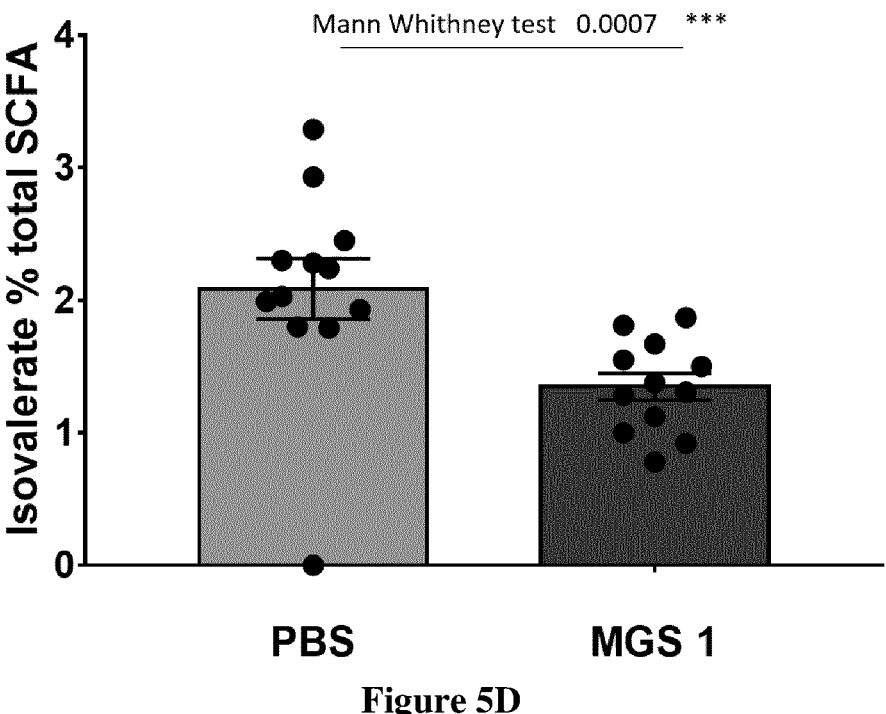
Figure 5E:
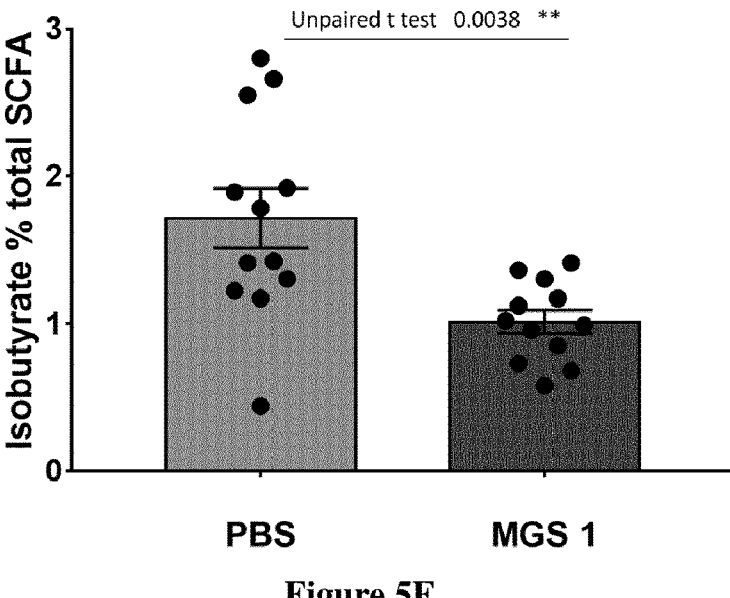

It was also observed that force-feeding with *A. equolifaciens* slowed hyperglycemia induced after 1 month (FIG. 4).

The gavage with *A. equolifaciens* also resulted in a reduction of the full caecum weight, an increase in the amount of butyrate produced and a reduction in the proportion of branched chain fatty acids (iso-butyrate and iso-valerate) (FIG. 5).

Figure 6A:
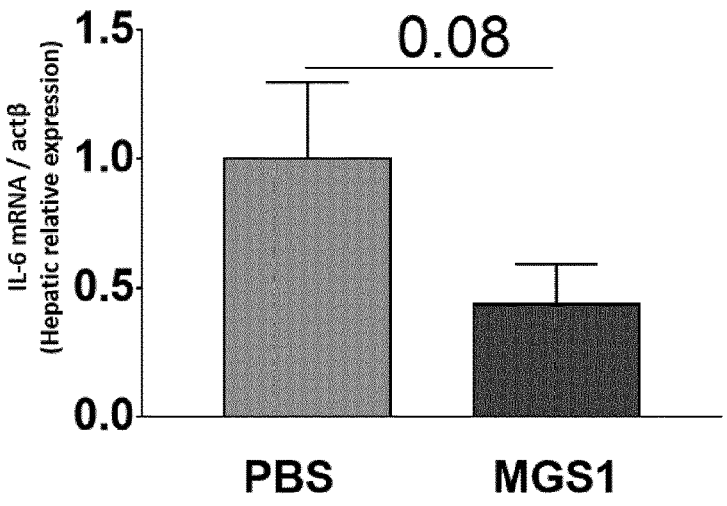
FIG. 6: *Adlercreutzia equolifaciens* gavage reduces IL-6 mRNA expression in the liver (A) and caecum (B) of mice. Actin is used as housekeeping gene in the liver and GAPDH in the caecum. Left, mean of mice receiving PBS as gavage. Right, mean of mice receiving *Adlercreutzia equolifaciens* (MGS1).
Figure 6B:
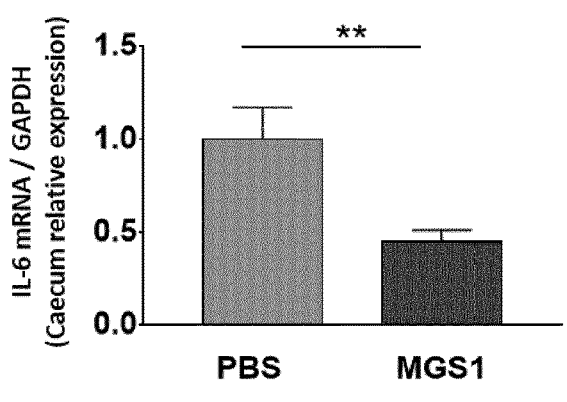

The gavage with *A. equolifaciens* further reduced the expression of a pro-inflammatory cytokine Interleukine-6 (IL-6) in the caecum and the liver (FIG. 6).

As a conclusion, it was shown that *A. equolifaciens* exerted anti-inflammatory effects in vitro, but also in vivo. This bacterium administered by gavage to mice in a model of hepatic steatosis induced by the transfer of gut microbiota from a NASH patient and subjected to a hyperlipidic, fructose-rich diet, induced a reduction in weight gain and some steatosis markers especially hyperglycemia and liver expression of the pro-inflammatory cytokine, interleukin-6.

Example 3

Materials and Methods

Cell Culture and Reagents

HT-29 intestinal epithelial cells in RPMI 1640 (Gibco) and HepG2 liver epithelial cells were grown in DMEM (Gibco) with 2 mM L-glutamine, 50 IU/mL penicillin, 50 μg/mL streptomycin and 10% heat-inactivated fetal calf serum (FCS—Lonza) in a humidified 5% $CO_2$ atmosphere at 37° C. Absence of *mycoplasma* contamination was controlled using the MycoAlert kit (Lonza).

Bacterial Strains and Preparation of Conditioned Media

*Adlercreutzia equolifaciens* (DSM 19450), *Adlercreutzia muris* (DSM 29508), *Adlercreutzia celatus* (*Adlercreutzia equolifaciens* subsp. *celatus* DSM 18785), *Adlercreutzia caecimuris* (DSM 21839), *Adlercreutzia musicola* (DSM 194950) and *Parvibacter caecicola* (DSM 22242) bacteria were grown in anaerobic M104 medium completed with 0.5% arginine at 37° C. using the Hungate culture method (Hungate RE (1950) Bacteriol Rev 14: 1-49).

At the end of the incubation period, DO of 0.3 or above, bacterial cultures were centrifuged at 5000 g for 10 minutes. Cell supernatant were collected and cell pellets were resuspended in 1 ml DPBS.

Analyses of NF-κB Activation—SEAP Reporter Assay

Construction and validation of the NF-κB reporter clones HT-29-NF-kB cl25 was described previously (Lakhdari et al, PLoS one, 2010). Construction and validation of the NF-KB reporter clones HepG2/kb-seap were done following the method described previously (Lakhdari et al, PLoS One 2010). For each experiment, reporter cells were seeded at 30 000 cells per well, into 96-wells plates and incubated 24 hours. Then cells were stimulated for 24 hours with 10 μl of tested resuspended bacterial pellet or supernatant, for a final volume of 100 μl per well (i.e. 10% vol/vol), in the presence or absence of TNF-α (10 ng/ml final). MG-132 (Millipore/Calbiochem used at a final concentration of 2.5 μmol/L) was used as a positive control of NF-kB pathway inhibition.

SEAP in the supernatant was revealed using the Quanti-Blue™ reagent (Invivogen) according to the manufacturer's protocol and quantified at $OD_{655nm}$. All measurements were performed using a microplate reader (Infinite 200, Tecan). Cell viability was controlled using the MTS assay (CellTiter 96 Aquous One, Promega) following manufacturer's instruction.

Statistical Analysis

Results are expressed as the mean±the standard error of the mean (SEM) of two experiments with triplicate determinations. The statistical analyses were performed using GraphPad Prism version 9 (GraphPad Software, San Diego, CA, USA). One-way ANOVA was carried out, followed by Dunnet's multiple comparisons test. p-values <0.05 were considered significant.

Results

Figure 7A:
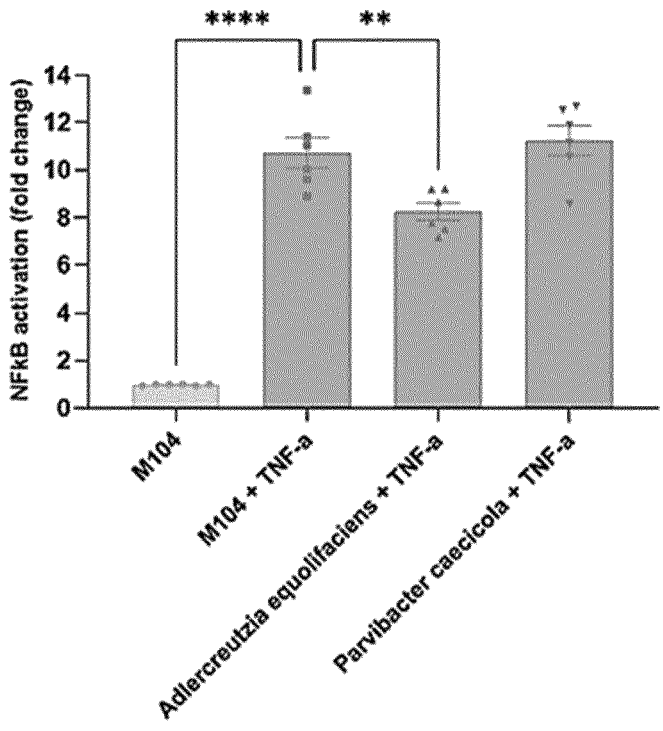
FIG. 7: (A) The supernatant of *Adlercreutzia equolifaciens* inhibited NF-KB activity on HT-29 NF-kB reporter cell lines. On the contrary, the supernatant of *Parvibacter caecicola* had no effect. NF-kB activity was measured in the absence (first bar) or presence of TNF-alpha. Values represent fold increase of NF-kB activity in unstimulated cells (M104). (B) The supernatants of *Adlercreutzia muris, Adlercreutzia celatus, Adlercreutzia caecimuris* and *Adlercreutzia musicola* inhibited NF-KB activity on HT-29 NF-kB reporter cell lines. NF-kB activity was measured in the absence (first bar) or presence of TNF-alpha. Values represent fold increase of NF-kB activity in unstimulated cells (M104). (C) Cell viability assay. HT-29 NF-kB cell viability was not affected by the treatment with TNF-alpha in the presence or absence of the supernatant of the bacterial strains. (D) The pellet of *Adlercreutzia equolifaciens* strongly inhibited NF-KB activity on HT-29 NF-kB reporter cell lines. On the contrary, the pellet of *Parvibacter caecicola* had no effect. NF-kB activity is measured in the absence (first bar) or presence of TNF-alpha. Values represent fold increase of NF-kB activity in unstimulated cells (PBS). (E) The pellets of *Adlercreutzia muris, Adlercreutzia celatus, Adlercreutzia caecimuris* and *Adlercreutzia musicola* inhibited NF-KB activity on HT-29 NF-kB reporter cell lines. NF-kB activity is measured in the absence (first bar) or presence of TNF-alpha. Values represent fold increase of NF-kB activity in unstimulated cells (PBS). (F) Cell viability assay. HT-29 NF-kB cell viability was not affected by the treatment with TNF-alpha in the presence or absence of the pellet of the bacterial strains. (G) The pellet of *Adlercreutzia equolifaciens* strongly inhibited NF-KB activity on HepG2 NF-KB reporter cell lines. On the contrary, the pellet of *Parvibacter caecicola* had no effect. NF-kB activity is measured in the absence (first bar) or presence of TNF-alpha. Values represent fold increase of NF-kB activity in unstimulated cells (PBS). (H) The pellets of *Adlercreutzia muris, Adlercreutzia celatus, Adlercreutzia caecimuris* and *Adlercreutzia musicola* inhibited NF-KB activity on HepG2 NF-KB reporter cell lines. NF-kB activity is measured in the absence (first bar) or presence of TNF-alpha. Values represent fold increase of NF-kB activity in unstimulated cells (PBS). (I) Cell viability assay. HepG2 NF-KB cell viability was not affected by the treatment with TNF-alpha in the presence or absence of the pellet of the bacterial strains.
Figure 7B:
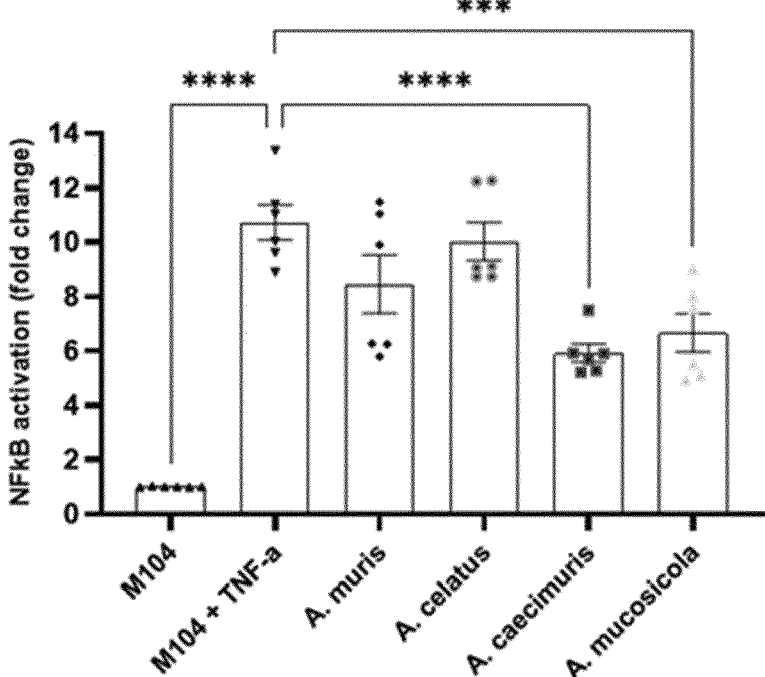
Figure 7C:
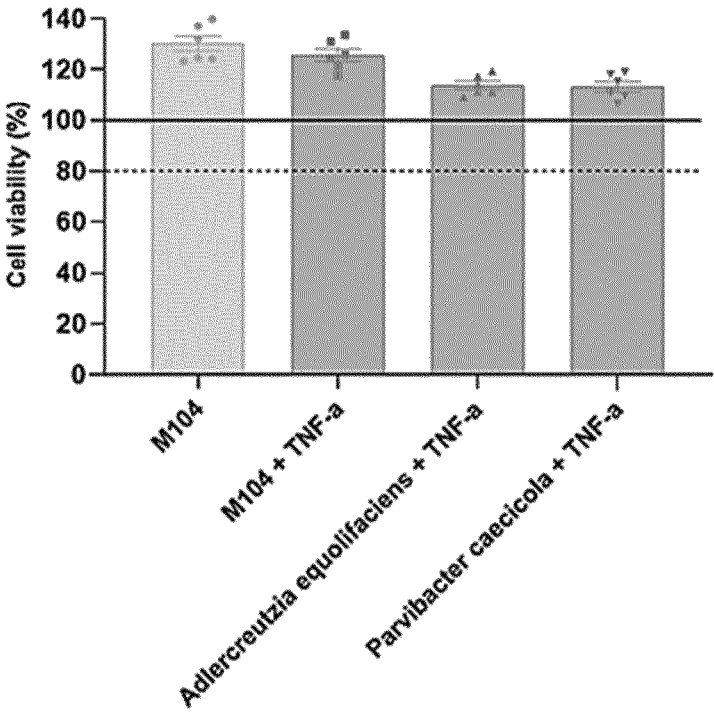

As illustrated on FIG. 7A, HT-29 NF-kB cells used in the test responded strongly to TNF-alpha by activating the NF-κB pro-inflammatory pathway by a fold >11. M104 (bacterial culture medium) in the absence of TNF was used as negative control. When incubated with TNF-alpha in the presence of the supernatant of *Adlercreutzia equolifaciens*, the fold activation was reduced to 8 indicating a mild inhibition. Similar results were obtained using other *Adlercreutzia* species including *A. muris, A. celatus, A. caecimuris* and *A. musicola* (FIG. 7B). In contrast, the supernatant of *Parvibacter caecicola*, a closely related member of the Eggerthellaceae family, had no effect on NF-kB activation following TNF-alpha stimulation. FIG. 7C showed that the culture medium and the supernatant of *Adlercreutzia equolifaciens* and *Parvibacter caecicola* had not statistical effect on cell viability as assessed measuring MTS activity.

Figure 7D:
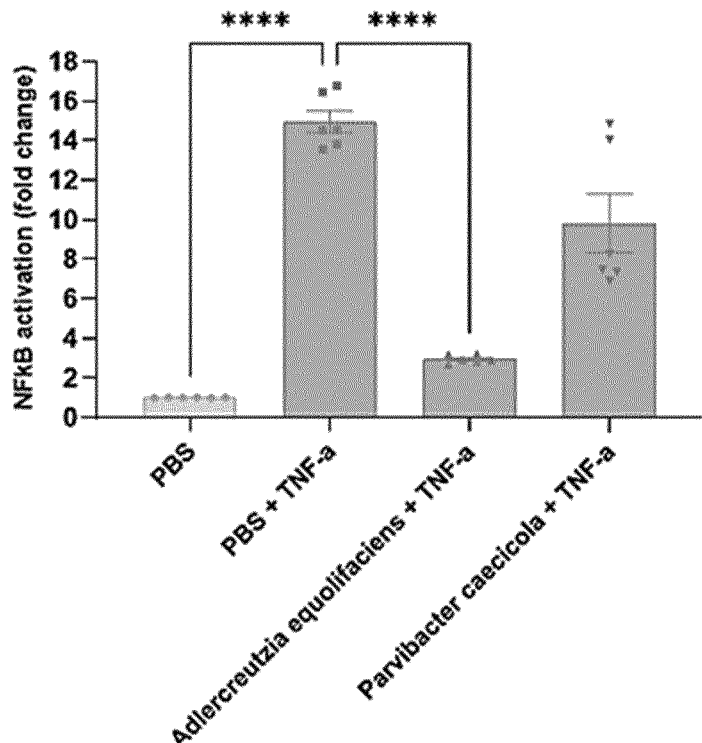
Figure 7E:
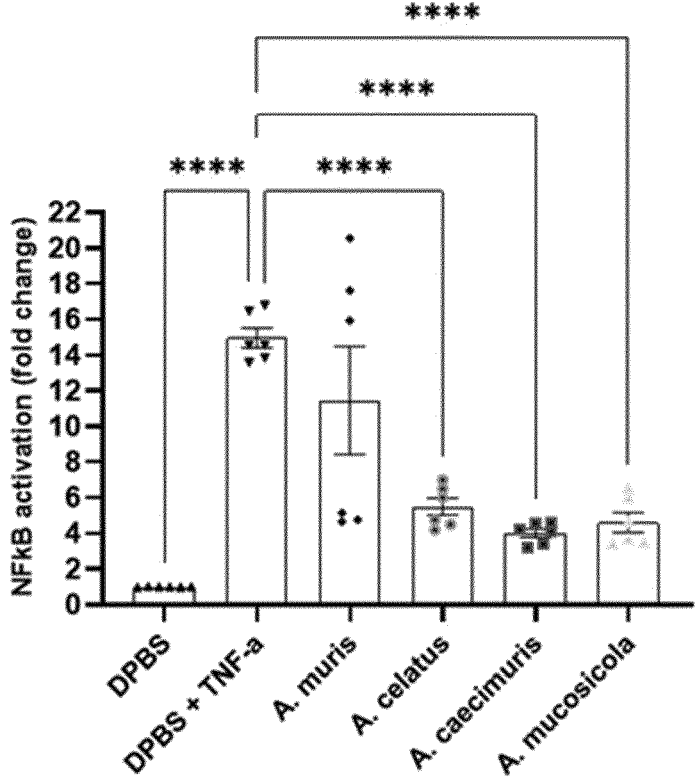
Figure 7F:
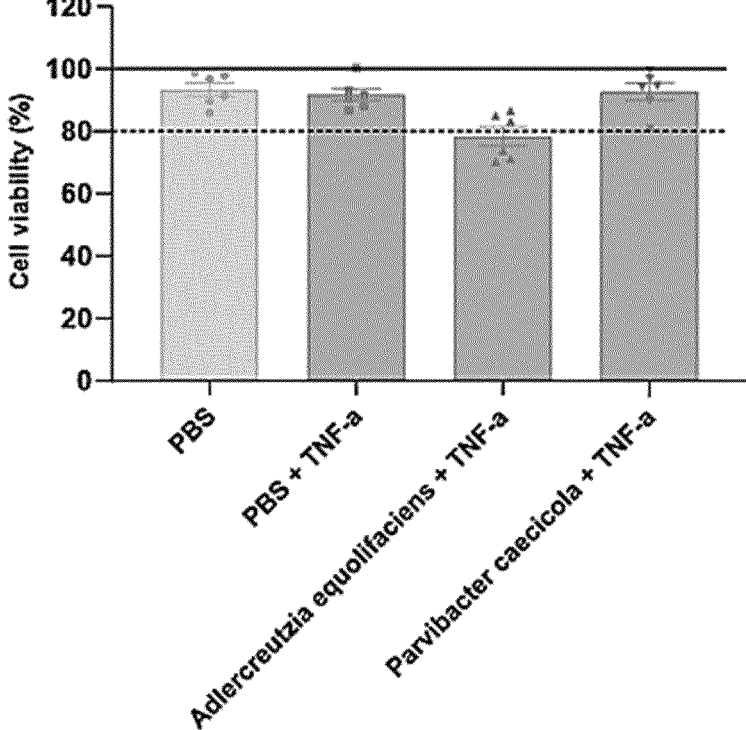
Figure 7G:
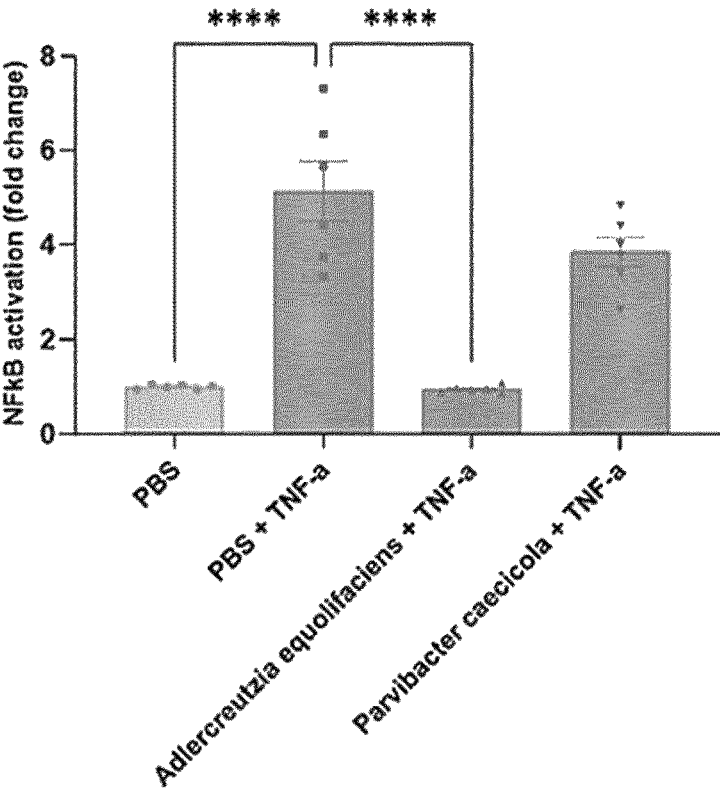

As illustrated on FIG. 7D, HT-29 NF-kB cells used in the test responded strongly to TNF-alpha by activating the NF-κB pro-inflammatory pathway by a fold >15. PBS used to resuspend bacterial pellet in the absence of TNF was used as negative control. When incubated with TNF-alpha in the presence of the pellet of *Adlercreutzia equolifaciens*, the fold activation was reduced to 2 indicating a strong inhibition. Similar results were obtained using other *Adlercreutzia* species including *A. muris, A. celatus, A. caecimuris* and *A. musicola* (FIG. 7E). In contrast, the pellet of *Parvibacter caecicola* had a mild and non-statistically significant effect on NF-kB activation following TNF-alpha stimulation. FIG. 1F showed that cell viability was not affected by the pellet of *Adlercreutzia equolifaciens* and *Parvibacter caecicola* as assessed measuring MTS activity.

On FIG. 1G it is shown that HepG2 NF-kB cells used in the test responded strongly to TNF-alpha by activating the NF-κB pro-inflammatory pathway by a fold of 5. PBS used to resuspend bacterial pellet in the absence of TNF was used as negative control. When incubated with TNF-alpha in the presence of the pellet of *Adlercreutzia equolifaciens*, the fold activation was strongly reduced to a level closed to non-activated cells. Similar results were obtained using other *Adlercreutzia* species including *A. muris, A. celatus, A.*

Figure 7H:
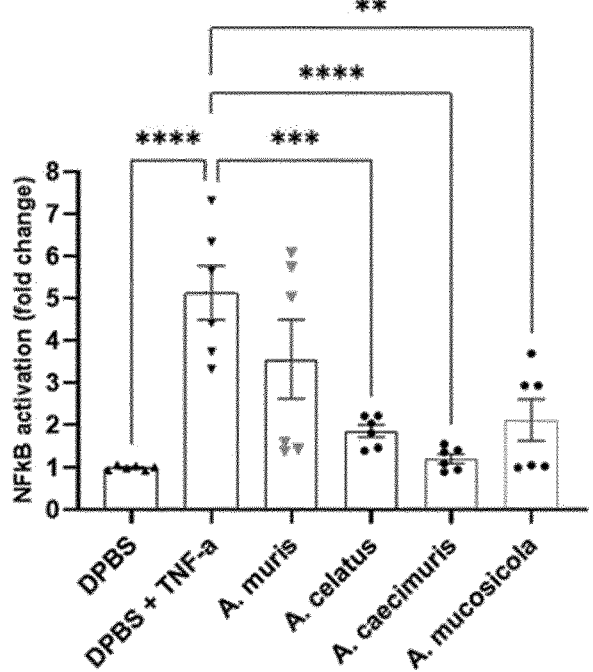
Figure 7I:
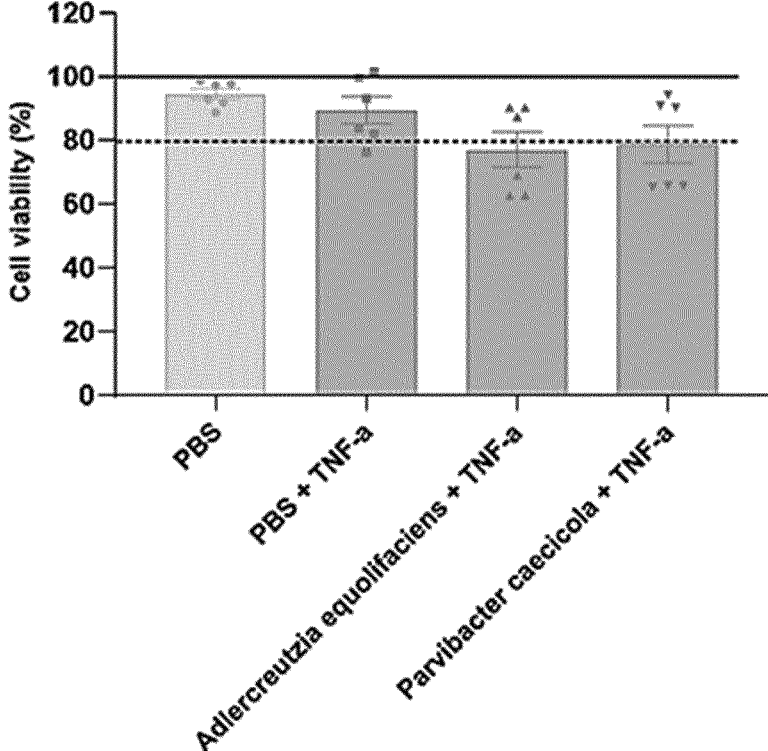

*caecimuris* and *A. musicola* (FIG. 7H). In contrast, the pellet of *Parvibacter caecicola* had no effect on NF-kB activation following TNF-alpha stimulation. FIG. 11 right showed that cell viability was not affected by the pellet of *Adlercreutzia equolifaciens* and *Parvibacter caecicola* as assessed measuring MTS activity.

These results highlight the anti-inflammatory potential of *Adlercreutzia* bacteria.

The invention claimed is:

1. A method of treating an inflammatory disease comprising administering a composition comprising an *Adlercreutzia* bacterium and/or a culture extract thereof to a subject having an inflammatory disease, wherein the *Adlercreutzia* bacterium is selected from the group consisting of *Adlercreutzia equolifaciens, Adlercreutzia caecimuris, Adlercreutzia mucosicola* and *Adlercreutzia muris*.

2. The method according to claim 1, wherein the *Adlercreutzia* bacterium is *Adlercreutzia equolifaciens*.

3. The method according to claim 1, wherein the composition comprises an *Adlercreutzia* bacterium selected from the group consisting of *Adlercreutzia equolifaciens, Adlercreutzia caecimuris, Adlercreutzia mucosicola* and *Adlercreutzia muris*.

4. The method according to claim 1, wherein the composition comprises a living *Adlercreutzia* bacterium selected from the group consisting of *Adlercreutzia equolifaciens, Adlercreutzia caecimuris, Adlercreutzia mucosicola* and *Adlercreutzia muris*.

5. The method according to claim 4, wherein the composition comprises a living *Adlercreutzia equolifaciens* bacterium.

6. The method according to claim 1, wherein the composition comprises a culture extract of said *Adlercreutzia* bacterium.

7. The method according to claim 6, wherein the culture extract is selected from the group consisting of culture supernatant, cell debris, cell walls and protein extracts.

8. The method according to claim 6, wherein the culture extract is culture supernatant.

9. The method according to claim 1, wherein the composition comprises several strains of *Adlercreutzia* and/or a culture extract of said strains of *Adlercreutzia*.

10. The method according to claim 1, wherein the composition further comprises at least one additional active ingredient.

11. The method according to claim 10, wherein said at least one additional active ingredient is an additional bacterial probiotic.

12. The method according to claim 1, wherein the composition further comprises or is used in combination with one or several drugs useful in the treatment of the inflammatory disease.

13. The method according to claim 1, wherein said composition is administered by an oral or rectal route.

14. The method according to claim 1, wherein the inflammatory disease is selected from the group consisting of non-alcoholic fatty liver disease and associated disorders and inflammatory bowel diseases.

15. The method according to claim 14, wherein the inflammatory disease is selected from non-alcoholic fatty liver disease or associated disorders, said disorders being selected from the group consisting of cholangitis, obesity, insulin resistance, glucose intolerance, type 2 diabetes and coronary heart diseases.

16. The method according to claim 14, wherein the inflammatory disease is a non-alcoholic fatty liver disease selected from the group consisting of non-alcoholic fatty liver (NAFL), non-alcoholic steatohepatitis (NASH), cirrhosis, liver failure and hepatocellular carcinoma.

17. The method according to claim 15, wherein the inflammatory disease is an associated disorder selected from the group consisting of cholangitis, obesity, insulin resistance, glucose intolerance, type 2 diabetes and coronary heart disease, and the subject to be treated is suffering from non-alcoholic fatty liver disease.

18. The method according to claim 17, wherein the non-alcoholic fatty liver disease is non-alcoholic steatohepatitis (NASH).

19. The method according to claim 14, wherein the inflammatory disease is an inflammatory bowel disease selected from the group consisting of Crohn's disease, colitis, enteritis and pouchitis.

20. The method according to claim 14, wherein the inflammatory bowel disease is ulcerative colitis or indeterminate colitis (IC).

21. The method according to claim 14, wherein the inflammatory bowel disease is a noninfective gastroenteritis.

* * * * *

SEQUENCE LISTING

```
<160> NUMBER OF SEQ ID NOS: 1

<210> SEQ ID NO 1
<211> LENGTH: 1458
<212> TYPE: DNA
<213> ORGANISM: Adlercreutzia equolifaciens

<400> SEQUENCE: 1
agagtttgat cctggctcag gatgaacgct ggcggcgtgc ttaacacatg caagtcgaac      60
gattaagacg gcttcggccg tgtatagagt ggcgaacggg tgagtaacac gtgaccaacc     120
tgccccgcgc tccgggacaa ccgctggaaa cggcggctaa taccggatgc tccggggagg     180
ccccatggcc tccccgggaa agccccgacg gcgcgggatg gggtcgcggc ccattaggta     240
gacggcgggg taacggccca ccgtgcccgc gatgggtagc cggactgaga ggtcgaccgg     300
ccacattggg actgagatac ggcccagact cctacgggag gcagcagtgg ggaattttgc     360
gcaatggggg caaccctgac gcagcaacgc cgcgtgcggg acgaaggcct tcgggttgta     420
aaccgctttc agcagggaag acatagacgg tacctgcaga agaagctccg gctaactacg     480
tgccagcagc cgcggtaata cgtaggggc gagcgttatc cggattcatt gggcgtaaag     540
cgcgcgtagg cggccgccta agcggaacct ctaatcccgg ggctcaacct cgggccgggt     600
tccggactgg gcggctcgag tgcggtagag gcaggcggaa ttcccggtgt agcggtggaa     660
tgcgcagata tcgggaagaa caccgatggc gaaggcagcc tgctgggccg ccactgacgc     720
tgaggcgcga aagctggggg agcgaacagg attagatacc ctggtagtcc cagccgtaaa     780
cgatggacgc taggtgtggg gggaccatcc ccccgtgccg cagccaacgc attaagcgtc     840
ccgcctgggg agtacggccg caaggctaaa actcaaagga attgacgggg gcccgcacaa     900
gcagcggagc atgtggctta attcgaagca acgcgaagaa ccttaccagg gcttgacatg     960
cgagtgaagc cgcggagacg cggtggccga gaggagctcg cgcaggtggt gcatggctgt    1020
cgtcagctcg tgtcgtgaga tgttgggtta agtcccgcaa cgagcgcaac ccccgtcccg    1080
tgttgccagc attcagttgg ggactcgcgg gagactgccg gcgtcaagcc ggaggaaggt    1140
ggggacgacg tcaagtcatc atgccccctta tgccctgggc tgcacacgtg ctacaatggc    1200
cggtacagag ggttgccacc ccgcgagggg gagcggatcc cggaaagccg gtcccagttc    1260
ggatcgcagg ctgcaacccg cctgcgtgaa gtcggagttg ctagtaatcg cggatcagca    1320
tgccgcggtg aatacgttcc cgggccttgt acacaccgcc cgtcacacca cccgagtcgt    1380
ctgcacccga agccgccggc cgaacccttc tggggcggag gcgtcgaagg tgtggagggt    1440 aagggggtg aagtcgta                                                  1458
```